United States Patent
Engel et al.

[11] 3,950,427
[45] Apr. 13, 1976

[54] ARALIPHATIC KETONES AND CARBINOLS
[75] Inventors: Wolfhard Engel; Josef Nickl; Helmut Teufel; Günther Engelhardt; Ernst Seeger; Günter Trummlitz, Biberach an der Riss, Germany
[73] Assignee: Boehringer Ingelheim GmbH, Ingelheim am Rhine, Germany
[22] Filed: Dec. 12, 1974
[21] Appl. No.: 532,174

[30] Foreign Application Priority Data
Dec. 17, 1973 Germany............................ 2362589
Oct. 26, 1974 Germany............................ 2450991

[52] U.S. Cl...... 260/590 D; 260/590 R; 260/590 C; 260/618 R; 260/618 D; 424/331; 424/343; 424/345; 260/599; 260/592; 260/484 R; 260/473 R; 260/343.5; 260/651 R; 260/348 A
[51] Int. Cl.² .................. C07C 49/76; C07C 49/80
[58] Field of Search................. 260/590, 591, 590 D

[56] References Cited
UNITED STATES PATENTS
3,702,343  11/1972  Beets et al. .......................... 260/590
3,859,256  1/1975   Teufel et al. ........................ 260/590
3,879,449  4/1975   Anderson et al. ............... 260/590 D Primary Examiner—Bernard Helfin
Assistant Examiner—James H. Reamer
Attorney, Agent, or Firm—Hammond & Littell

[57] ABSTRACT
Compounds of the formula

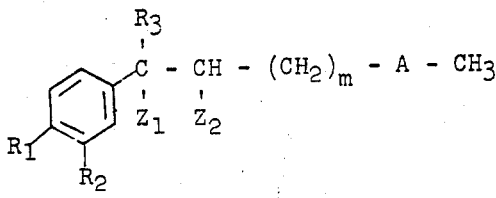

wherein
$R_1$ is isobutyl, phenyl, o-fluoro-phenyl, o-chloro-phenyl, cyclopentyl, cyclohexyl, methyl-cyclo-hexyl or cycloheptyl,
$R_2$ is hydrogen, fluorine, chlorine or bromine,
$R_3$ is methyl, ethyl or, when $R_1$ is phenyl, fluoro-phenyl or chloro-phenyl, or $R_1$ is cyclohexyl and $R_2$ is halogen, also hydrogen,
$Z_1$ and $Z_2$ are hydrogen or together form an additional carbon-to-carbon bond,
A is

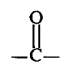

or

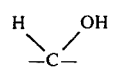

and
m is 2, 4, 6, 8 or when $R_1$ is halo-phenyl, isobutyl, cyclohexyl, methyl-cyclohexyl, cyclopentyl or cycloheptyl and/or $R_2$ is halogen and/or $R_3$ is methyl or ethyl and/or A is —CH(OH)—, also 0; the compounds are useful as antiphlogistics.

7 Claims, No Drawings

ARALIPHATIC KETONES AND CARBINOLS

This invention relates to novel araliphatic ketones and carbinols, as well as to various methods of preparing these compounds.

More particularly, the present invention relates to a novel class of araliphatic ketones and carbinols represented by the formula

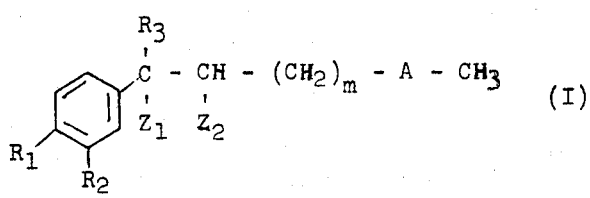

wherein
$R_1$ is isobutyl, phenyl, o-fluoro-phenyl, o-chloro-phenyl, cyclopentyl, cyclohexyl, methyl-cyclohexyl or cycloheptyl,
$R_2$ is hydrogen, fluorine, chlorine or bromine,
$R_3$ is methyl, ethyl or, when $R_1$ is phenyl, fluoro-phenyl or chloro-phenyl, or $R_1$ is cyclohexyl and $R_2$ is halogen, also hydrogen,
$Z_1$ and $Z_2$ are hydrogen or together form an additional carbon-to-carbon bond,
A is

or

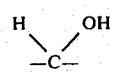

and
$m$ is 2,4,6,8 or when $R_1$ is halo-phenyl, isobutyl, cyclohexyl, methyl-cyclohexyl, cyclopentyl or cycloheptyl and/or $R_2$ is halogen and/or $R_3$ is methyl or ethyl and/or A is —CH(OH)—, also 0.

Among the olefinic compounds embraced by formula I, those which are E-configurated with respect to the carbon-to-carbon double bond are of particular interest.

The compounds of the formula I above may be prepared by the following methods:

METHOD A

Broadly, by reaction of a metalorganyl with a suitable compound comprising a multiple C-X-bound (X being defined below), and subsequent hydrolysis; and more particularly 1. by reacting a metalorganyl of the formula $$M - CH_3 \qquad (II)$$

with a compound of the formula

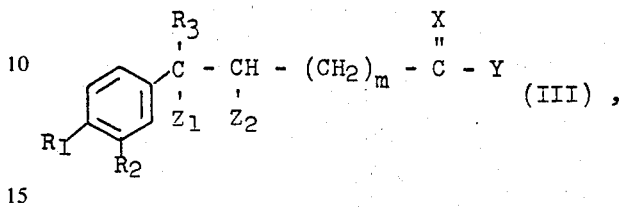

or (2) by reacting a metalorganyl of the formula

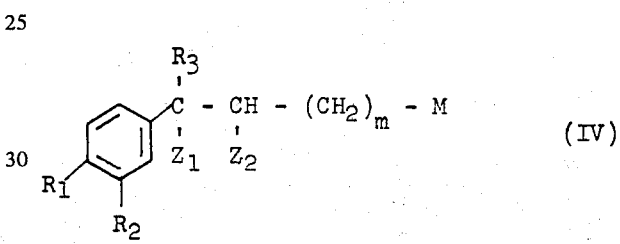

with a compound of the formula

In formulas II, III, IV and V,
$R_1, R_2, R_3, Z_1, Z_2$ and m have the same meanings as in formula I,
M is lithium or -MgHal, where Hal is chlorine, bromine or iodine, and
X is oxygen when Y is hydrogen or amino, or X is nitrogen when Y is an additional bond between C and X.
When the

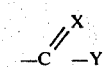

moiety in compounds of the formula III or V represents —CO—NH$_2$ or cyano, their reaction with a compound of the formula II or IV, respectively, and subsequent hydrolysis yield a biphenyl derivative of the formula I wherein A is —CO—. On the other hand, if the

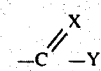

moiety in compounds of the formula III or V represents —CH=O, a compound of the formula I wherein A is —CH(OH)— is obtained as the end product, provided the metalorganyl is supplied at least in stoichiometric quantitative ratio or in excess thereover; however, if an aldehyde of the formula III or V is made available in excess for this reaction, the reaction between the metalorganyl and the carbonyl compound per se is followed by an oxidation by the excess aldehyde, which is catalyzed by the metal alcoholate which is formed, so that subsequent hydrolysis yields a mixture of a ketone and an alcohol of the formula I, that is, a mixture of corresponding compounds wherein A is —CO— and —CH(OH)—, respectively. This mixture may thereafter be used to isolate, by means of the reduction or oxidation processes described under methods C and D below, the individual components of the formula I, that is, the alcohol and the ketone.

The reaction of a metalorganyl of the formula II or IV with a compound of the formula III or V, respectively, is performed at a temperature between $-80°$ and $+100°C$, preferably between $-40°$ and $+60°C$, and advantageously in the presence of an ether solvent, such as diethyl ether, tetrahydrofuran, dioxane, ethyleneglycol dimethyl ether or anisole, optionally in admixture with an aromatic hydrocarbon, such as benzene or toluene. The reaction may also be performed in an aliphatic hydrocarbon solvent, such as n-pentane, n-hexane or n-heptane. A carboxylic acid amide of the formula III or V is advantageously reacted in the presence of methylene chloride, preferably at a temperature between $30°$ and $50°C$.

METHOD B

Broadly, for the preparation of a compound of the formula I wherein $Z_1$ and $Z_2$ are hydrogen, by hydrogenating a correspondingly substituted compound of the formula I wherein $Z_1$ and $Z_2$ together form an additional carbon-to-carbon bond; and more particularly 1. by catalytic hydrogenation in the presence of a conventional catalyst, especially in the presence of a finely divided metal of sub-group VIII of the Periodic System, such as Raney cobalt, Raney nickel, palladized charcoal, palladized barium sulfate, platinum or platinum(IV)oxide. The hydrogenation is discontinued after absorption of 1 to 1.2 mols of hydrogen per mol of starting compound. Suitable solvents include carbinols, such as methanol, ethanol or isopropanol; aromatic hydrocarbons, such as benzene; ethers, such as dioxane; esters of lower alkanoic acids, such as methyl acetate or ethyl acetate; or mixtures of any two or more of the aforementioned solvents. The hydrogenation is carried out at a temperature between $0°$ and $40°C$, preferably at room temperature, and at a pressure of 0 to 100 atmospheres gauge, preferably 1 to 5 atmospheres gauge.

If the starting material is a compound of the formula I wherein $Z_1$ and $Z_2$ together form an additional carbon-to-carbon bond and A is —CO—, the carbonyl group is, as a rule, partially reduced simultaneously with the olefinic bond. The resulting reaction product is a mixture of the corresponding ketone and carbinol of the formula I wherein $Z_1$ and $Z_2$ are hydrogen, which may readily be converted into its respective components by the reduction or oxidation procedures described under methods C and D below, so that a uniform end product of the formula I is obtained wherein A is either —CO— or —CH(OH)—. The mixture of ketone and carbinol may, however, also be separated into its individual components by column chromatography.

The simultaneous partial reduction of the carbonyl group A does not occur, however, if colloidal nickel boride (P-2 catalyst), which is obtained by reduction of nickel(II) acetate with sodium borohydride in ethanol, is used as the hydrogenation catalyst; or 2. by reduction with nascent hydrogen of a compound of the formula I wherein $Z_1$ and $Z_2$ together form an additional carbon-to-carbon bond and A is —CO—. The reduction may be effected with sodium amalgam in an acid medium, accompanied by careful dropwise addition of dilute acetic acid to maintain acid conditions; or with zinc amalgam in a mixture of ethanol and aqueous acetic acid at a temperature between $60°C$ and the boiling point of the solvent mixture.

The saturation of the olefinic double bond may also be effected by electrolytic reduction in a substantially neutral or acid medium. For example, the particular $\alpha,\beta$-unsaturated ketone of the formula I may be electrolytically reduced in acetic acid in the presence of dilute sulfuric acid in the cathode chamber of an electrolytic cell the anode chamber of which is filled with aqueous 20% sulfuric acid. The cathode of such a cell may be a lead cylinder or mercury layer of about 1 cm thickness, and the anode may be a lead or carbon rod. The electrolysis may, however, also be performed by using a mixture of ethyl acetate, ethanol, water and potassium acetate as the cathode liquid.

Finally, the saturation of the olefinic bond in an $\alpha,\beta$-unsaturated ketone of the formula I may also be effected by heating it with an aqueous titanium(III)halide, preferably titanium(III)chloride, in an aqueous-ethanolic ammonia solution on a steam bath.

METHOD C

For the preparation of a compound of the formula I wherein A is —CH(OH)—, by reducing a correspondingly substituted compound of the formula I wherein A is —CO—, or by reducing a ketone/carbinol mixture obtained pursuant to methods A or B. The reduction may be effected 1. by means of a complex hydride. Suitable complex hydrides include alkali metal or alkaline earth metal aluminum hydrides, such as lithium aluminum hydride, sodium aluminum hydride or magnesium aluminum hydride; alkoxy aluminum hydrides, such as sodium bis-(2-methoxy-ethoxy)-dihydroaluminate, lithium trimethoxyaluminum hydride or lithium tris-(tert.butoxy)-aluminum hydride; alkali metal or alkaline earth metal borohydrides and alkoxyborohydrides, such as lithium borohydride, sodium borohydride, calcium borohydride, lithium cyanoborohydride, sodium cyanoborohydride, sodium methoxyborohydride or zinc borohydride; or combinations of lithium aluminum hydride or sodium borohydride with a Lewis acid, especially with aluminum chloride or borontrifluoride.

If the starting compound of the formula I is one wherein $Z_1$ and $Z_2$ are both hydrogen, the reduction may also be performed with diborane. The diborane need not be provided as such; it may also be generated in situ in the solution in which the reduction is carried out, such as by reacting sodium borohydride in diethyleneglycol dimethyl ether with sulfuric acid, chlorosulfonic acid, methanesulfonic acid, phosphoric acid, a boron halide, zinc(II)chloride, mercury(I) chloride, aluminum chloride, anhydrous hydrogen chloride or the like.

The reduction is carried out in a suitable solvent medium, preferably in an ether, such as tetrahydrofuran, diethyl ether, 1,2-dimethoxy-ethane, diethyleneglycol dimethyl ether or triethyleneglycol dimethyl ether; or also in an aromatic hydrocarbon, such as benzene; or in a mixture of any two or more of the aforesaid solvents. The reduction with sodium borohydride, sodium cyanoborohydride or sodium trimethoxyborohydride may alsobe performed in a lower alkanol, preferably in ethanol, or in an alcohol/water mixture. Depending upon the particular complex hydride which is used, the operative reaction temperature lies between −80° and +100°C, but a temperature between 0° and +30°C is preferred.

In general, the geometric configuration of the substituents attached to an olefinic carbon atom remains the same during the reduction with a complex hydride, although a partial isomerization is sometimes observed, so that a mixture of the Z- and E-isomers is occasionally obtained after working up the reaction mixture. Or 2. by means of a primary or secondary alcohol in the presence of an alcoholate of a metal of the 1st to 3rd main groups of the Periodic System; for example, in isopropanol in the presence of aluminum isopropylate, magnesium isopropylate, sodium ethylate or aluminum dichloroisopropylate. This reduction is preferably carried out in an aromatic hydrocarbon solvent, such as in benzene or toluene, and at elevated temperatures, preferably at the boiling point of the particular solvent medium which is used, while continuously distilling the ketone, such as acetone, formed by the reaction out of the reaction mixture. The reduction may, however, also be performed in the absence of the primary or secondary alcohol, that is, with a metal alcoholate by itself, for example with molten aluminum isopropylate, or with aluminum isopropylate in toluene solution. Or 3. by the action of a non-noble metal in an alkaline medium. Examples of suitable non-noble metals include sodium, sodium amalgam, calcium, magnesium, zinc, zinc amalgam, aluminum and aluminum amalgam. Examples of suitable solvents include lower alkanols, such as methanol or ethanol, moist ether or moist benzene. The reduction is carried out at a temperature between room temperature and the boiling point of the particular solvent which is used.

A variation of this process consists of reducing the ketone starting compound with sodium in liquid ammonia and in the presence of an excess of ammonium chloride.

If $R_3$ in the starting ketone of the formula I is halogen, it should be expected that this halogen atom will be entirely or partially replaced by hydrogen under all conditions of a reduction with non-noble metals, also, olefinic double bonds which may be present in the starting compound are saturated thereby. Therefore, the end product obtained by this reduction process will always be a compound of the formula I wherein $Z_1$ and $Z_2$ are both hydrogen. Or 4. by catalytic hydrogenation. A number or different catalysts are suitale for this method of reduction, namely platinum from hexachloroplatinic acid, from ammonium hexachloroplatinate or from platinum(IV)oxide; Raney nickel, palladium-on-charcoal; copper-barium-chromoxide; ruthenium-or rhodium-on-charcoal, or copper chromite. The hydrogenation is carried out under alkaline, neutral or acid conditions in a suitable solvent. Examples of such solvents are alcohols; mixtures of water and alcohols; ethers, such as dioxane; ethyl acetate, or lower aliphatic carboxylic acids, such as glacial acetic acid or trifluoroacetic acid. If one of the above-mentioned metal catalysts is used, the hydrogenation is carried out at a temperature between 20° and 100°C, but preferably above +40°C; the oxidic catalysts require a temperature between 100° and 250°C.

In the case of carbonyl starting compounds of the formula I wherein $Z_1$ and $Z_2$ form a double bond, the corresponding saturated ketone is first formed, and only thereafter is the carbonyl group reduced to the carbinol group by a second mol of hydrogen. Or 5. by reduction with thiourea-S,S-dioxide. The reduction is performed in aqueous-ethanolic solution in the presence of a caustic alkali, preferably at the boiling point of the solvent medium. The reducing agent is advantageously provided in excess over the stoichiometrically required amount, namely up to 3.0 mols per mol of substrate to be reduced. 2 Mols of alkali metal hydroxide are advantageously provided per mol of reducing agent.

METHOD D

For the preparation of a compound of the formula I wherein A is —CO—, by oxidizing a correspondingly substituted compound of the formula I wherein A is —CH(OH)—, or by oxidizing a ketone/carbinol mixture obtained pursuant to method A or B. The oxidation may be effected 1. with a chromium(VI)compound. Examples of particularly suitable such chromium compounds are sodium dichromate, potassium dichromate, chromium(VI)oxide and di(tert.butyl)-chromate. The oxidation may be carried out in a number of different solvent media, such as in water, glacial acetic acid, acetone, petroleum ether, benzene, tetrachloromethane, pyridine, dimethylformamide or mixtures thereof, and at a temperature of 0° to 100°C, preferably at room temperature or moderately elevated temperatures.

Particularly advantageous is the oxidation with a. chromium(VI)oxide or an alkali metal dichromate in aqueous sulfuric acid solution, and advantageously in the presence of glacial acetic acid and optionally also benzene as additional solvents;

b. chromium(VI)oxide or an alkali metal dichromate in glacial acetic acid;

c. chromium(VI)oxide in pyridine;

d. chromium(VI)oxide in aqueous sulfuric acid solution in the presence of acetone;

e. di(tert.butyl)chromate in a non-polar solvent, such as petroleum ether, tetrachloromethane or benzene; or f. chromium(VI)oxide in dimethylformamide in the presence of concentratd sulfuric acid.

2. with manganese(IV)oxide. This process is especially well suited for the oxidation of α,β-unsaturated carbinols of the formula I wherein $Z_1$ and $Z_2$ together form an additional carbon-to-carbon bond. It is advantageous to use a large excess of the oxidizing agent. Preferred solvent media are petroleum ether, acetone, diethyl ether or tetrahydrofuran, but benzene, chloroform ir tetrachloromethane may alternatively be used as solvents. The oxidation is preferably performed at a temprature between 0° and 100°C, but preferably at room temperature; the oxidation of an α,β-unsaturated carbinol of the formula I ($Z_1$ and $Z_2$ form a double bond) may also be performed at the boiling point of the particular solvent which is used.

3. with a ketone in the presence of an alcoholate of a metal of the 1st to 3rd main group of the Periodic System. Examples of suitable catalysts are aluminum alcoholates of the carbinol which is to be oxidized, aluminum phenolate, aluminum isopropylate or, most preferably, aluminum tert. butylate. Examples of suitable ketones, which act as hydrogen acceptors, are acetone, 1,4-benzoquinone or cyclohexanone. Benzene or toluene is advantageously provided as an additional solvent medium. The oxidation is preferably carried out at elevated temperatures up to and including the boiling point of the solvent medium, and with a large excess of the hydrogen acceptor.

4. with anhydrous dimethylsulfoxide in the presence of N,N′-dicyclohexyl-carbodiimide and an acid agent. Suitable acid agents are primarily medium strong inorganic or organic acids, such as anhydrous phosphoric acid, phosphorous acid, cyanoacetic acid, pyridinium phosphate or pyridinium sulfate; especially suitable are dichloroacetic acid or pyridinium trifluoroacetate. The acid agent is preferably provided in an amount corresponding to 0.5 mol per mol of carbinol of the formula I to be oxidized; however, it may also be provided in lesser or greater quantity, for example 0.1 or 1.0 mol per mol of carbinol. The dicyclohexyl-carbodiimide is advantageously provided in excess of at least 2 mols per mol of carbinol, and preferably in a quantitative ratio of 3 mols per mol of carbinol. After completion of the oxidation, the excess, unreacted dicyclohexyl carbodiimide is removed from the reaction mixture by addition of oxalic acid, which quickly reacts with the carbodiimide to form carbon dioxide, carbon monoxide and N,N′-dicyclohexyl-urea. Because of its sparse solubility in most organic solvents, the dicyclohexyl-urea may easily be separated from the desired oxidation product. The amount of dimethylsulfoxide required for the oxidation is at least an equimolar amount, based on the carbinol to be oxidized.

It is often advantageous to add a co-solvent to the reaction mixture, especially one which is immiscible with water, such as benzene or ethyl acetate. This auxiliary measure has the effect of improving the inherently limited solubility of dicyclohexyl-carbodiimide in dimethylsulfoxide; moreover, the reaction is less exothermic under these conditions, because it is performed in less concentrated solution.

Other substituted carbodiimdes may also be used in place of N,N′-dicyclohexyl-carbodiimide, such as N,N′-diisopropyl-carbodiimide, N,N′-diethyl-carbodiimide, N,N′-di-(p-tolyl)-carbodiimide or N-cyclohexyl-N′-(p-toluenesulfonyl)-carbodiimide, but the use of these carbodiimides, which split off water and activate the dimethylsulfoxide in such oxidation reactions, offers no significant advantage over the use of N,N′-dicyclohexyl-carbodiimide. Similarly, other compounds which resemble the carbodiimides in their mechanism of action and also catalyze oxidations with dimethylsulfoxide, are suitable, such as N-ethyl-5-phenyl-isoxazolium-3′-sulfonate, trichloroacetonitrile, ethoxy-acetylene or diphenylketene-p-tolylimine. The oxidation with dimethylsulfoxide may also carried out in the presence of an inorganic or organic acid anhydride, such as acetic acid anhydride, benzoic acid anhydride, phosphorus pentoxide, polyphosphoric acid or pyridine-anhydrosulfuric acid.

Other sulfoxides, such as tetramethylenesulfoxide, may also be used in place of dimethylsulfoxide. Or 5. with 2,3-dichloro-5,6-dicyano-1,4-benzoquinone in an inert organic solvent, such as dioxane, anisole, benzene, toluene or mixtures thereof, at a temperature between 10°C and the boiling point of the particular solvent medium which is used.

METHOD E

For the preparation of a compound of the formula I wherein $R_3$ is hydrogen, $Z_1$ and $Z_2$ together form an additional carbon-to-carbon bond, A is —CO—, and $m$ is zero, 1. by subjecting an aldehyde of the formula

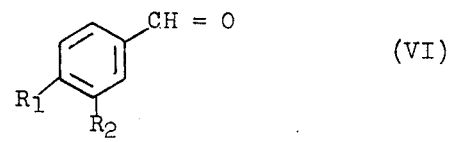

(VI)

wherein $R_1$ and $R_2$ have the same meanings as in formula I, to a condensation reaction with acetone.

The reaction is catalyzed by a base. Examples of suitable basic catalysts are ethanolic or aqueous solutions of alkali metal or alkaline earth metal hydroxides, especially aqueous sodium or potassium hydroxide, aluminum alcoholates, piperidine acetate or basic ionexchangers. In order to exclude a reaction of the acetone with two molecules of the aldehyde of the formula VI, the acetone is advantageously provided in 3- to 100-fold excess. Water or a lower alkanol of 1 to 3 carbon atoms, or a mixture thereof, may be added to the reaction mixture as a supplemental solvent. The condensation reaction is performed at a temperature from −10° to +50°C, preferably between 20° and 25°C.

In accordance with a variation of this process, the condensation is performed with zinc oxide as the catalyst, at a temperature between 150° and 200°C, preferably from 170° to 190°C, at an elevated pressure of 10 to 300 atmospheres, preferably at 50 atmospheres, and in an atmosphere of an inert gas, preferably nitrogen.

Acid agents, especially mineral acids, are also suitable as catalysts for the condensation reaction, especially hydrogen chloride or hydrogen bromide, or aqueous or ethanolic solutions thereof.

In the reaction products of this method and its variations, that is, in the compounds of the formula I where $R_3$ is hydrogen, A is —CO—, $m$ is zero, and $Z_1$ and $Z_2$ together form an additional carbon-to-carbon bond, the aryl and acetyl radicals are E-configured with respect to the olefinic double bond. Or 2. by reacting an aldehyde of the formula VI with triphenylphosphine acetylmethylene of the formula $$(C_6H_5)_3P=CH-\overset{O}{\underset{\|}{C}}-CH_3 \qquad (VII)$$

preferably in an ethereal solvent medium, such as tetrahydrofuran, ethyleneglycol dimethyl ether or dimethyleneglycol dimethyl ether, at a temperature between 50° and 120°C, preferably between 60° and 80°C.

As s rule, the reaction is carried out under careful exclusion of moisture. However, the reaction will also proceed in the presence of water if it is carried out as a Micell Reaction or under phase transfer catalysis, for instance in the presence of a suitable tetra-substituted ammonium salt. The isolation of triphenylphosphine acetylmethylene of the formula VII is thereby obviated; instead, the aldehyde of the formula VI is reacted directly with an acetonyl-triphenylphosphonium salt of the formula $$(C_6H_5)_3\overset{(+)}{\underset{X^{(-)}}{P}}-CH_2-\overset{O}{\underset{\|}{C}}-CH_3 \qquad (VIII)$$

wherein X is halogen, in a benzolic-aqueous alkaline medium. As a rule, the employment of an excess of the acetonyl-triphenylphosphonium salt is advantageous. However, the reaction may also be performed with a stoichiometric amount or less than a stoichiometric amount of the onium salt. At least an equimolar amount, based on the acetonyl-triphenylphosphonium salt, of an alkali metal or alkaline earth metal hydroxide or alkali metal carbonate is provided. In place of benzene, another water-immiscible solvent may be used, such as toluene, xylene, chlorobenzene, o-dichlorobenzene, pentane, hexane, petroleum ether, gasoline or the like.

An aldehyde of the formula VI may also be reacted with a phosphonate anion of the formula $$\left[(R_5O)_2\overset{O}{\underset{\|}{P}}\cdots CH\cdots \overset{O}{\underset{\|}{C}}-CH_3\right] \qquad (VIIa)$$

wherein $R_5$ is lower alkyl, instead of with a triphenylphosphine acetylmethylene of the formula VII. The requisite phosphonate anion is obtained in situ by the action of a strong base upon a phosphonate of the formula $$(R_5O)_2\overset{O}{\underset{\|}{P}}-CH_2-\overset{O}{\underset{\|}{C}}-CH_3 \qquad (VIIb)$$

wherein $R_5$ has the meaning defined above, in the presence of an aprotic, anhydrous solvent. Examples of suitable strong bases are alkali metal alcoholates, such as sodium methylate, potassium methylate, sodium ethylate or potassium tert.butylate; alkali metal amides, such as sodium amide or sodium diisopropylamide; or alkali metal hydrides, such as sodium hydride or lithium hydride. Examples of suitable aprotic solvents are ethyleneglycol dimethyl ether, diethyleneglycol dimethyl ether, triethyleneglycol dimethyl ether, tetrahydrofuran, dimethylformamide or hexamethylphosphoric acid triamide. The operative reaction temperature range is between 0° and 100°C, preferably between 20° and 80°C.

A phosphonate of the formula VIIb may be obtained by reacting a corresponding trialkylphosphite with bromoacetone [see N. Kreutzkamp et al., *Chem. Berichte* 89, 1614–1619 (1956)].

METHOD F

For the preparation of a compound of the formula I wherein $Z_1$ and $Z_2$ together form an additional carbon-to-carbon bond, A is —CO— and m is zero, by subjecting an aldehyde of the formula VI or a ketone of the formula (IX)

wherein
$R_1$ and $R_2$ have the same meanings as in formula I, and
$R_3$ is methyl or ethyl,
to a condensation reaction with a crotonic acid ester of the formula (X)

wherein
$R_6$ and $R_7$, which may be identical to or different from each other, are alkyl of 1 to 4 carbon atoms, cycloalkyl of 5 to 7 carbon atoms, aryl or aralkyl of no more than 10 carbon atoms.

The condensation is carried out under anhydrous conditions and in the presence of a strong base, such as an alkali metal alcoholate, preferably potassium methylate or potassium tert.butylate, as well as in the presence of a dipolar aprotic solvent, such as hexamethylphosphoric acid triamide or dimethylformamide, or in the presence of an alkali metal amide, such as lithium amide, preferably in liquid ammonia.

The initially formed intermediate of the formula (XI)

or a salt thereof, or a cyclic tautomer thereof of the formula

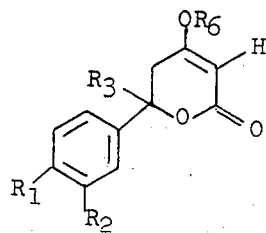

(XII)

wherein $R_1$, $R_2$, $R_3$ and $R_6$ have the meanings previously defined, are subsequently de-carboxylated.

In a preferred embodiment of this method, the initially formed intermediate of the formula XI or XII is not isolated, but instead, after the condensation reaction has gone to completion, concentrated hydrochloric acid is added to the reaction mixture and the acid mixture is heated briefly at 80° to 100°C, whereby the desired end product is obtained with good yields by a single-vessel procedure.

The metalorganyls of the formula II and the compounds of the formula V, which are needed as starting compounds in method A, are described in the literature.

The compounds of the formula III wherein Y is hydrogen are obtained by known methods, for example by reduction of a corresponding nitrile. The nitrile is, for instance, reduced with an equivalent amount of a complex hydride, such as lithium aluminum tri-tert-.butoxyhydride or lithium triethoxyaluminum hydride, in a solvent such as tetrahydrofuran at a temperature between −70° and +20°C; the aldehyde is subsequently liberated by hydrolysis with water or a dilute acid [see H. C. Brown et al., *Tetrahedron Letters* 3, 9 (1959)].

A compound of the formula III wherein X is oxygen, Y is —NH$_2$, $Z_1$ and $Z_2$ are hydrogen and m is zero, may be obtained by reacting a compound of the formula

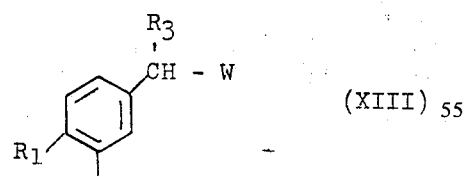

(XIII)

wherein
  $R_1$ and $R_2$ have the same meanings as in formula I, and
  W is hydroxyl, halogen or acyloxy,
with 1,1-dichloroethylene in sulfuric acid, and subsequently hydrolyzing the initially formed intermediate by addition of water. The carboxylic acid thus obtained is then converted into its acid chloride which, in turn, is converted into the corresponding acid amide of the formula III with the aid of ammonia.

A compound of the formula III wherein X is oxygen, Y is —NH$_2$, and $Z_1$ and $Z_2$ together form a double bond, may be obtained by reacting a ketone of the formula IX or an aldehyde of the formula VI with a zinc compound of an α-halocarboxylic acid ester to form an ester of the formula

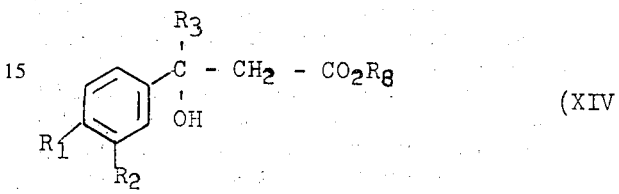

(XIV)

wherein
  $R_1$, $R_2$ and $R_3$ have the same meanings as in formula I, and
  $R_8$ is lower alkyl.

This reaction is carried out in an organic solvent, such as an ether, benzene or toluene, at a temperature between 20° and 60°C. The ester of the formula XIV is thereafter treated with a dehydrating agent in a water-immiscible, inert solvent at a temperature up to and including the boiling point of the reaction mixture, and advantageously in a vessel equipped with a water trap. Examples of suitable dehydrating agents are salts of pyridine or of alkylpyridines formed with hydrohalic acids, potassium bisulfate, zinc chloride, phosphorus oxyhalides, p-toluenesulfonic acid, sulfuric acid or phosphoric acid. Examples of suitable solvents are benzene, toluene or xylene. The unsaturated ester formed thereby is subsequently converted with ammonia into the corresponding compound of the formula III wherein Y is —NH$_2$, X is oxygen, and $Z_1$ and $Z_2$ together form a double bond, from which a corresponding nitrile of the formula III can be obtained by dehydration.

The saturated nitriles embraced by formula III, that is, when X is nitrogen, Y is an additional bond between the carbon atom and X, $Z_1$ and $Z_2$ are hydrogen, and $R_1$, $R_2$ and $R_3$ have the meanings previously defined, may be prepared by reacting a compound of the formula

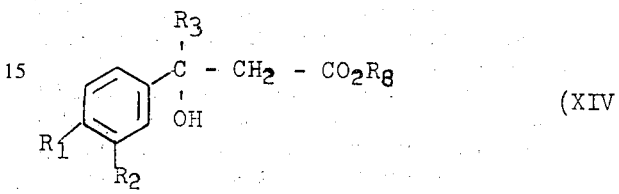

(XV)

wherein
  $R_1$, $R_2$ and $R_3$ have the same meanings as in formula I, and
  Hal is halogen, preferably bromine, with sodium cyanide. These nitriles may, in turn, by hydrolized into the corresponding carboxylic acids of the formula

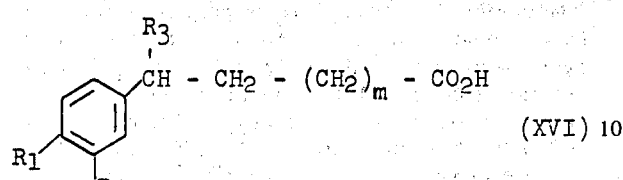

(XVI)

wherein $R_1$, $R_2$, $R_3$ and $m$ have the same meanings as in formula I. These carboxylic acids may then be reduced with lithium aluminum hydride in ether to form the corresponding alcohols, which are subsequently reacted with a phosphorus(III)halide to form compounds which correspond to those of the formula XV, except that the side chain is lengthened by one methylene group. From these homologous compounds the next higher homologous nitriles may be obtained by reaction with potassium cyanide, and by repeating this sequence of steps several times, all of the nitriles of the formula III wherein m is other than zero are readily accessible.

The compounds of the formula XV may themselves be prepared by reacting a correspondingly substituted phenylalkane with an ethoxyalkyl chloride and anhydrous aluminum chloride to form the corresponding 2-(substituted phenyl)-glyoxylic acid ester which is hydrolized and then reacted with one mol-equivalent of an alkylmagnesium bromide to give the corresponding 2-(substituted phenyl)-2-hydroxy-alkanoic acid. The corresponding 2-(substituted phenyl)-alkanoic acid may be obtained therefrom by treatment with hydrogen iodide in clacial acetic acid, and subsequent reduction of the acid with lithium aluminum hydride in ether yields to a phenylalkanol of the formula

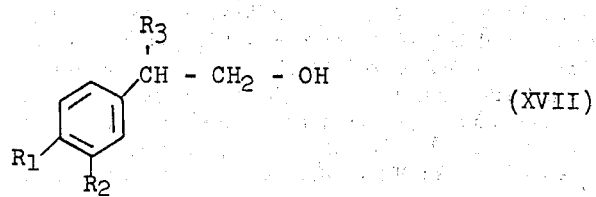

(XVII)

wherein $R_1$, $R_2$ and $R_3$ have the same meanings as in formula I, which is converted into the corresponding compound of the formula XV by heating with a phosphorus trihalide, such as phosphorus tribromide.

The metalorganyls of the formula IV can be prepared by known methods from the corresponding halo-substituted compounds of the formula

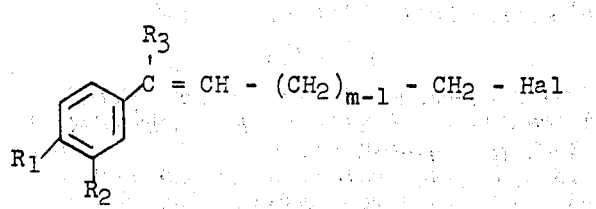

(XVIII)

wherein $R_1$, $R_2$, $R_3$ and $m$ have the meanings previously defined.

A compound of the formula XVIII, in turn, may be obtained by heating a compound of the formula

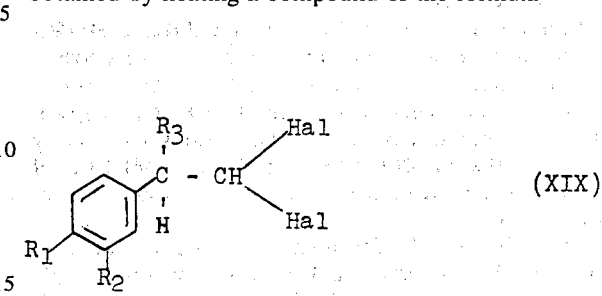

(XIX)

wherein $R_1$, $R_2$ and $R_3$ have the same meanings as in formula I, and

Hal is chlorine or bromine, with a strong alkali, such as by heating it with ethanolic sodium hydroxide at 120°C.

A compound of the formula XIX may itself be prepared by reacting an aldehyde of the formula

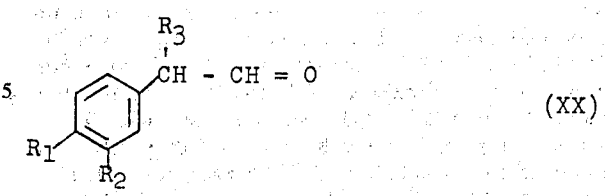

(XX)

wherein $R_1$, $R_2$ and $R_3$ have the same meanings as in formula I, with a phosphorus(V)halide.

A compound of the formula XX may be prepared by hydrolysis of a glycide ester of the formula

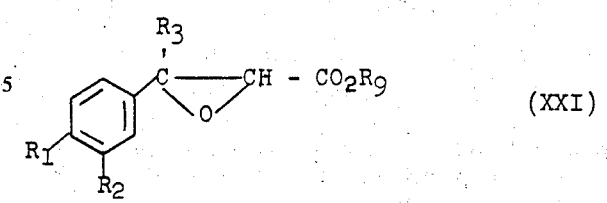

(XXI)

wherein

R₁, R₂ and R₃ have the same meanings as in formula I, and

R₉ is lower alkyl, with hot aqueous-ethanolic sodium hydroxide, acidification of the reaction mixture to form the corresponding glycidic acid, and de-carboxylation of the latter.

The glycide esters of the formula XXI may be prepared by methods described in the literature, such as by reacting a ketone of the formula IX or an aldehyde of the formula VI with a chloroacetic acid ester and sodium amide.

An aldehyde of the formula VI may be obtained, for example, by subjecting a ketone of the formula IX wherein R is methyl to a haloform reaction. The substituted benzoic acid of the formula

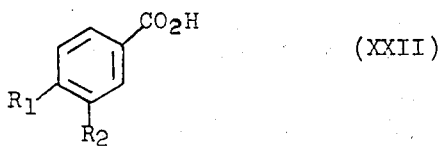

(XXII)

wherein R₁ and R₂ have the same meanings as in formula I, obtained thereby is then reduced with lithium aluminum hydride in boiling ether or boiling tetrahydrofuran to form the corresponding benzyl alcohol which, by oxidation with freshly prepared manganese(II)oxide [see E. F. Pratt et al., *J. Org. Chem.* 26, 2973 (1961)] or with 70% nitric acid [see A. McKillop et al., *Synth. Commun.* 2, 307 (1972)], smoothly converts into the desired aldehyde of the formula VI.

The compound of the formula VII may easily be obtained by the method of F. Ramirez et al., *J. Org. Chem.* 22, 41 (1957), i.e. by the action of a base on an acetyl-triphenylphosphonium salt of the formula VIII which, in turn, is prepared by reacting a halo-acetone with triphenylphosphine.

A ketone of the formula IX wherein R₂ is hydrogen may be obtained in simple fashion by reacting a correspondingly substituted benzene of the formula

(XXIII)

wherein R₁ has the meanings previously defined, with acetyl or propionyl chloride in the presence of anhydrous aluminum chloride.

The ketones of the formula IX wherein R₂ is halogen may be prepared, for example, by diazotizing a correspondingly 4-substituted 3-amino-alkanophenole in a hydrohalic acid medium, and reacting the diazotization product with a solution of copper(I)halide in a hydrohalic acid. However, a chlorinated ketone of the formula IX may also be prepared directly from a ketone of the formula IX wherein R₂ is hydrogen by reacting it with chlorine in the presence of aluminum chloride; for instance, 3'-chloro-4'-cyclohexyl-acetophenone, b.p. 135°–139°C at 1.5 mm Hg, $n_D^{20} = 1.5617$, was prepared in this manner.

The starting compounds of the formula IX wherein R₁ is unsubstituted phenyl may be prepared by diazotizing a 3'-halo-4'-amino-acetophenone or a corresponding propiophenone and subsequently reacting the diazotization product with benzene in the presence of sodium hydroxide or sodium acetate; for instance, 4-acetyl-2-chloro-biphenyl, m.p. 42°–44°C, b.p. 134°–142°C at 1.5 mm Hg, was prepared in this manner. These starting compounds may, however, also be synthesized by reacting a methyl magnesium halide with a 4-cyano-2-halo-biphenyl, followed by hydrolysis of the ketimine magnesium halide intermediate; for instance, 4-acetyl-2-fluoro-biphenyl, m.p. 97°–98°C, was prepared in this manner.

The starting compounds of the formula X are accessible by reaction of an acetoacetate with an orthoformate in the presence of a catalytic amount of sulfuric acid.

The following examples illustrate the present invention and will enable others skilled in the art to understand it more completely. It should be understood, however, that the invention is not limited solely to the particular examples given below.

EXAMPLE 1

(E)-4-(2'-Fluoro-4-biphenylyl)-3-buten-2-one by method E 200.2 Gm (1.0 mol) of 2'-fluoro-4-biphenyl-carboxaldehyde, 3500 gm (60.3 mols) of acetone and 200 ml of methanol were charged into a 6-liter three-neck flask equipped with a stirrer, a dropping funnel and an internal thermometer. While thoroughly stirring the contents of the flask, a solution of 2.805 gm (0.05 mol) of potassium hydroxide in 16 ml of water was added dropwise thereto while maintaining a reaction temperature of 20° to 25°C, and the resulting mixture was stirred for three hours more. Thereafter, the precipitated solid side product was filtered off, the filtrate was made neutral by dropwise addition of glacial acetic acid, and the neutral solution was evaporated in vacuo. The residue was recrystallized three times from diisopropyl ether and then once from a mixture of ethyl acetate and diisopropyl ether (volumetric ratio 1:1) in the presence of activated charcoal, yielding 101.2 gm (42% of theory) of the fallow crystalline compound of the formula

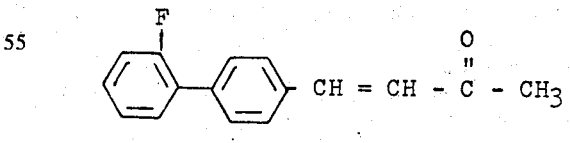

which had a melting point of 113°–114°C.

EXAMPLE 2

Using a procedure analogous to that described in Example 1, 56% of theory of fallow crystalline (E)-4-(2'-chloro-4-biphenylyl)-3-buten-2-one, m.p. 124°–125°C after recrystallization from diisopropyl ether in the presence of activated charcoal, was obtained from 2'-chloro-4-biphenyl-carboxaldehyde and acetone.

EXAMPLE 3

Using a procedure analogous to that described in Example 1, 31% of theory of fallow crystalline (E)-4-(2-fluoro-4-biphenylyl)-3-buten-2-one, m.p. 82°–83°C after three recrystallizations from diisopropyl ether, was obtained from 2-fluoro-4-biphenyl-carboxaldehyde and acetone.

EXAMPLE 4

Using a procedure analogous to that described in Example 1, 52% of theory of fallow crystalline (E)-4-(2-chloro-4-biphenylyl)-3-buten-2-one, m.p. 70°–72°C after recrystallization from ethanol, was obtained from 2-chloro-4-biphenyl-carboxaldehyde and acetone.

EXAMPLE 5

(E)-4-(2-Fluoro-4-biphenylyl)-3-penten-2-one by method F 72.8 Gm (0.649 mol) of potassium tert.butylate were added all at once to a slution of 97.0 gm (0.453 mol) of 4-acetyl-2-fluoro-biphenyl and 103.0 gm (0.651 mol) of (E)-3-ethoxy-crotonic acid ethyl ester in 1 liter of anhydrous dimethylformamide, whereby the temperature of the mixture rose spontaneously from 20°C to 38°C and its color turned intensely red. The reaction mixture was stirred for one hour while maintaining an internal temperature of 32° to 35°C, and then, while the mixture was still warm, 200 ml of concentrated hydrochloric acid were added dropwise thereto, and the resulting mixture was heated for 30 minutes at 90°–100°C. After the evolution of carbon dioxide had ceased, the cooled mixture was stirred into one liter of ice water, and the yellowish precipitate formed thereby was filtered off, thoroughly washed with water and recrystallized, in the presence of activated charcoal, once from methanol and twice from diisopropyl ether. 75.0 gm (65% of theory) of the fallow crystalline compound, m.p. 103°C, of the formula

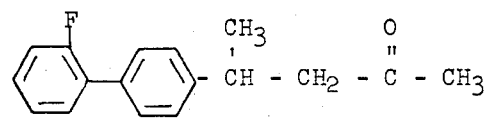

were obtained.

EXAMPLE 6

Using a procedure analogous to that described in Example 5, 50% of theory of fallow crystalline (E)-4-(2'-chloro-4-biphenylyl)-3-penten-2-one, m.p. 80°–81°C after recrystallization from cyclohexane and petroleum ether, was obtained from 4-acetyl-2'-chloro-biphenyl and (E)-3-ethoxy-crotonic acid ethyl ester.

EXAMPLE 7

Using a procedure analogous to that described in Example 5, 62% of theory of fallow crystalline (E)-4-(4-biphenylyl)-3-penten-2-one, m.p. 130°–132°C (from isopropanol), was obtained from 4-acetyl-biphenyl and (E)-3-ethoxy-crotonic acid ethyl ester.

EXAMPLE 8

4-(2'-Fluoro-4-biphenylyl)-2-pentanone by method A

A solution of 25.7 gm (0.1 mol) of 3-(2'-fluoro-4-biphenylyl)-butyramide in 750 ml of dry methylene chloride was added dropwise over a period of one hour to a methyl magnesium iodide solution which was prepared from 12.2 gm (0.5 mol) of magnesium and 71 gm (0.5 mol) of methyl iodide in a total of 400 ml of anhydrous ether, and the resulting mixture was refluxed for 6 hours to make the reaction go to completion. After cooling, the reaction mixture was stirred into a mixture consisting of 2 kg of ice and 100 ml of concentrated sulfuric acid. The ethereal phase was separated, washed twice with water, once with an aqueous saturated sodium bicarbonate solution, and again with water, dried over anhydrous magnesium sulfate and evaporated in vacuo. The solid residue was recrystallized twice from gasoline (b.p. range 60° to 80°C), yielding 22.0 gm (86% of theory) of the colorless crystalline compound, m.p. 60°–61°C, of the formula

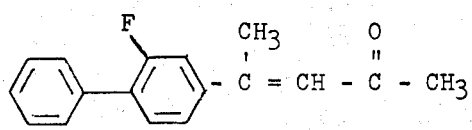

EXAMPLE 9

Using a procedure analogous to that described in Example 8, 78% of theory of 4-(2'-chloro-4-biphenylyl)-2-pentanone, a colorless highly viscous oil with a b.p. of 134°–137°C at 0.03 mm Hg, was obtained from 3-(2'-chloro-4-biphenylyl)-butyramide and methyl magnesium iodide.

EXAMPLE 10

(E)-4-(2'-Fluoro-4-biphenylyl)-3-penten-2-one by method A

A solution of 23.7 gm (0.1 mol) of 3-(2'-fluoro-4-biphenylyl)-crotononitrile in 500 ml of dry methylene chloride was added dropwise over a period of 75 minutes to a Grignard reagent prepared from 12.2 gm (0.5 mol) of magnesium and 71 gm (0.5 mol) of methyl iodide in 500 ml of anhydrous ether, and the resulting mixture was refluxed for 4.5 hours. Thereafter, the cooled reaction mixture was stirred into a mixture consisting of 2 kg of ice and 100 ml of concentrated sulfuric acid. The organic phase was separated, washed with aqueous 1% sulfuric acid, then with water, then with a saturated aqueous sodium bicarbonate solution and again with water, dried over sodium sulfate, and evaporated in vacuo. The solid residue was recrystallized from cyclohexane, yielding 7.2 gm (28% of theory) of fallow crystalline (E)-4-(2'-fluoro-4-biphenylyl)-3-penten-2-one, m.p. 92°C.

EXAMPLE 11

4-(2'-Fluoro-4-biphenylyl)-2-butanol by method A

A solution of 5.82 gm (0.132 mol) of acetaldehyde in 10 ml of dry ether was added dropwise to a stirred Grignard reagent prepared under exclusion of air from 47.0 gm (0.168 mol) of 1-bromo-2-(2'-fluoro-biphenylyl)-ethane and 4.0 gm (0.165 mol) of magnesium in 60 ml of anhydrous ether. All of these operations were carried out in an atmosphere of very pure nitrogen. The resulting mixture was heated for 2 hours on a water bath, while stirring, then cooled and hydryolized by addition of 50 gm of crushed ice, and subsequently half-concentrated hydrochloric acid was added until the precipitate which had formed just went into solution again. The ethereal phase was separated, the aqueous phase was extracted twice with ether, and the ethereal extracts were combined with the ethereal phase, washed with water, with an aqueous saturated sodium bicarbonate solution and again with water, dried over sodium sulfate and evaporated. The residue was recrystallized twice from petroleum ether in the presence of activated charcoal, yielding 9.0 gm (28% of theory) of the colorless crystalline compound of the formula

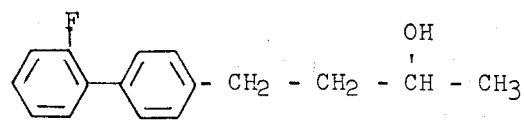

which had a melting point of 59°–60°C.

EXAMPLE 12

6-(4-Biphenylyl)-2-hexanol

A Grignard reagent prepared from 84.0 gm (0.29 mol) of 1-(4-biphenylyl)-4-bromo-butane and 7.08 gm (0.291 mol) of magnesium was reacted with 14.2 gm (0.32 mol) of acetaldehyde in absolute ether in a manner analogous to that described in Example 11. The mixture of 6-(4-biphenylyl)-2-hexanol and 6-(4-biphenylyl)-2-hexanone thus obtained (yield: 57 gm; about 77% of theory) was dissolved in one liter of ethanol, the resulting solution was admixed with a solution of 4.20 gm (0.112 mol) of sodium borohydride in 300 ml of ethanol, and the mixture was stirred at room temperature for one hour. Thereafter, the excess sodium borohydride was destroyed by addition of 6 ml of glacial acetic acid, the solution was evaporated, the residue was taken up in 500 ml of water, and the aqueous mixture was exhaustively extracted with ether. The combined ethereal extracts were dried over sodium sulfate, evaporated, the residue was taken up in petroleum ether, and the resulting solution was chromatographed on a total of 2 kg of silicagel, using first a mixture of petroleum ether and ethylene chloride (volumetric ratio 1:1) and later a mixture of ethylene chloride and ethyl acetate (volumetric ratio 8:2) as eluants. The principal product was taken up in ether, the solution was treated with activated charcoal and evaporated, and the residue was recrystallized from petroleum ether in the presence of activated charcoal, yielding 38.0 gm (52% of theory) of colorless crystalline 6-(4-biphenylyl)-2-hexanol, m.p. 71°–72°C.

EXAMPLE 13

Using a procedure analogous to that described in Example 11, 29% of theory of colorless crystalline 6-(2'-fluoro-4-biphenylyl)-2-hexanol, m.p. 52°–53°C after chromatography on silicagel with benzene/ethylene acetate (volumetric ratio 98:2) as the eluant and two recrystallizations from petroleum ether, was obtained from acetaldehyde and the Grignard reagent formed by 1-bromo-4-(2'-fluoro-4-biphenylyl)-butane and magnesium.

EXAMPLE 14

Using a procedure analogous to that described in Example 11, 42% of theory of colorless crystalline 8-(2'-fluoro-4-biphenylyl)-2-octanol, m.p. 64°–65°C (from petroleum ether), was obtained from acetaldehyde and the Grignard reagent formed by 1-bromo-6-(2'-fluoro-4-biphenylyl)-hexane and magnesium.

EXAMPLE 15

Using a procedure analogous to that described in Example 11, 69% of theory of colorless crystalline 12-(4-biphenylyl)-2-dodecanol, m.p. 84°–85°C (from petroleum ether), was obtained from acetaldehyde and the Grignard reagent formed by 1-(4-biphenylyl)-10-bromo-decane and magnesium.

EXAMPLE 16

4-(2'-Fluoro-4-biphenylyl)-2-pentanol by method A

A solution of 96.9 gm (0.4 mol) of 3-(2'-fluoro-4-biphenylyl)-butanal (b.p. 112°–114°C at 0.04 mm Hg) in 200 ml of anhydrous ether was added dropwise to a stirred solution of 0.5 mol of methyl magnesium bromide in 200 ml of ether, and the resulting mixture was heated for two hours on a water bath, while stirring. Thereafter, the reaction mixture was cooled, then hydrolized by addition of 50 gm of crushed ice, and subsequently an aqueous 50% ammonium chloride solution was added until the initially formed precipitate dissolved again. The ethereal phase was separated, the aqueous phase was extracted twice with ether, the ethereal extracts were combined with the ether phase, thoroughly washed with water and dried over sodium sulfate, the ether was distilled off, and the residue was distilled in a high vacuum. 55.8 Gm (54% of theory) of a mixture of diastereoisomers of 4-(2'-fluoro-4-biphenylyl)-2-pentanol was obtained as a colorless oil having a boiling point of 122° –124°C at 0.06 mm Hg.

EXAMPLE 17

4-(2'-Fluoro-4-biphenylyl)-2-butanone by method B

15 Gm (0.06 mol) of nickel(II)acetate tetrahydrate, dissolved in 600 ml of 95% ethanol, were reduced to black, colloidal nickel boride (P-2-catalyst) in a hydrogenation vessel with 60 ml of 1 M sodium borohyride solution in an atmosphere of hydrogen. In order to remove any unreacted borohydride which may be present, 14 gm (0.24 mol) of acetone were first added and the mixture was shaken for one hour at room temperature. Thereafter, 30.0 gm (0.123 mol) of (E)-4-(2'-fluoro-4-biphenylyl)-3-buten-2-one were added, and the mixture was hydrogenated at room temperature and 5 atmospheres until the absorption of hydrogen terminated. Subsequently, the catalyst was filtered off, the filtrate was evaporated in vacuo, and the residue was shaken with a mixture of water and ethyl acetate. The organic phase was dried over sodium sulfate and then evaporated, and the residue was distilled in a high vacuum, yielding 18.5 gm (62% of theory) of 4-(2'-fluoro-4-biphenylyl)-2-butanone in the form of a colorless, viscous oil having a boiling point of 153°–155°C at 0.4 mm Hg which solidified after prolonged standing and then had a melting point of 30°C.

EXAMPLE 18

4-(2'-Fluoro-4-biphenylyl)-2-butanol by method C 24.5 Gm (0.101 mol) of (E)-4-(2'-fluoro-4-biphenylyl)-3-butene-2-ol, dissolved in 300 ml of ethyl acetate, were hydrogenated at room temperature at a hydrogen pressure of 3 atmospheres in the presence of 8.5 gm of Raney-nickel until hydrogen absorption was complete. The catalyst was filtered off, the filtrate was evaporated in vacuo, and the residue was recrystallized twice from cyclohexane/petroleum ether (ratio by volume: 1:1). Yield: 15.0 gm (61% of theory) of colorless crystals, m.p. 59°–60°C.

EXAMPLE 19

4-(2'-Chloro-4-biphenylyl)-2-butanol was prepared analogous to Example 18 from (E)-4-(2'-chloro-4-biphenylyl)-3-butene-2-ol with a yield of 33%. The product was obtained as a colorless, non-crystallizing oil and was purified by chromatography on silica gel by use of, first benzene, then benzene/ethyl acetate (ratio of volume: 9:1) as eluant. The characterization was effected by IR-, UV- and NMR-spectra as well as by elemental analysis:

$C_{16}N_{17}Cl\ O$ (260.8): Calculated: C — 73.70%; H — 6.57%; Cl — 13.60%. Found: C — 73.70%; H — 6.70%; Cl — 13.30%.

EXAMPLE 20

4-(2-Fluoro-4-biphenylyl)-2-butanol was prepared analogous to Example 19 from (E)-4-(2-fluoro-4-biphenylyl)-3-butene-2-ol with a yield of 89% of theory. After recrystallizing twice from petroleum ether, the colorless crystals melted at 40°–42°C.

EXAMPLE 21

4-(2-Fluoro-4-biphenylyl)-2-pentanone was prepared analogous to Example 17 from (E)-4-(2-fluoro-4-biphenylyl)-3-pentene-2-one with a yield of 80% of theory. The colorless crystals melted at 85°–86°C (diisopropyl ether).

EXAMPLE 22

4-(2-Fluoro-4-biphenylyl)-2-butanone was prepared analogous to Example 17 from (E)-4-(2-fluoro-4-biphenylyl)-3-butene-2-one with a yield of 62% of theory. The colorless crystals melted at 41°–42°C after recrystallizing twice from petroleum ether.

EXAMPLE 23

4-(2-Chloro-4-biphenylyl)-2-butanone was prepared analogous to Example 17 from (E)-4-(2-chloro-4-biphenylyl)-3butene-2-one with a yield of 68% of theory as a colorless, highly viscous oil, b.p. 148°–153°C at 0.05 mm Hg.

EXAMPLE 24

4-(2-Fluoro-4-biphenylyl)-2-pentanol was prepared analogous to Example 19 from (E)-4-(2-fluoro-4-biphenylyl)-3-pentene-2-ol with a yield of 45% of theory. The colorless crystals melted at 53°–54°C after recrystallization from pletroleum ether in the presence of charcoal. After H-NMR-spectroscopical examination, only one of the two possible diastereomers was found to be present. From the mother liquors a non-crystallizing mixture of both diastereomers (colorless, highly viscous oils) could be isolated, again with a yield of 29% of theory.

EXAMPLE 25

(E)-4-(4-Biphenylyl)-3-butene-2-ol by method C 13.0 Gm (0.0585 mol) of (E)-4-(4-biphenylyl)-3-butene-2-one were gently refluxed with 12.5 gm (0.0612 mol) of aluminum-isopropoxide and 190 ml (2.48 mol) of isopropanol in a dry distillation apparatus with a 60-cm-Vigreux-column, in such a way that only about 5 drops were distilled off per minute. After about 5 hours no acetone was found to be present in the distillate (by use of hydrochloric 2,4-dinitrophenylhydrazine-solution). In the reaction mixture, column-chromatography showed no starting material was present. The isopropanol was distilled off in a weak vacuum, the residue was hydrolyzed by addition of 50 gm of crushed ice and 34 ml of 6 N hydrochloric acid. The reaction mixture was exhaustively extracted with ethyl acetate, the combined extracts were washed with water, with 5% sodium hydroxide solution and again with water, and dried over sodium sulfate. The solvent was evaporated in vacuo and the residue was recrystallized, once from cyclohexane/ethyl acetate (ratio by volume: 9:1) and once from benzene. Yield: 11.0 gm (84% of theory) of colorless crystals, m.p. 138°–139°C.

EXAMPLE 26

(E)-4-(4-Biphenylyl)-3-butene-2-ol by method C 22.2 Gm (0.1 mol) of (E)-4-(4-biphenylyl)-3-butene-2-one, dissolved in 1 liter of 95% ethanol, were added in small amounts within 10 minutes to a solution of 1.9 gm (0.05 mol) of sodium borohydride in 300 ml of 95% ethanol. Subsequently, the mixture was stirred for 1 hour at room temperature. The excess reducing agent was removed by careful addition of 3 gm of glacial acetic acid. The solvent was subsequently distilled off in water aspirator vacuum. 500 Ml of water were added to the residue, and the reaction mixture was exhaustively extracted with ether. The combined ether extracts were washed with water, dried over sodium sulfate and evaporated. The residue was recrystallized from ethyl acetate/petroleum ether (ratio of volume: 1:9) in the presence of charcoal. 16.1 Gm (72% of theory) of colorless crystals, m. p. 138°–139°C, were obtained; the compounds was completely identical with that prepared in Example 25 according to thin-layer chromatogram, melting point, mixed melting point and spectra.

EXAMPLE 27

4-(4-Biphenylyl)-2-butanol was prepared analogous to Example 26 from 4-(4-biphenylyl)-2-butanone with a yield of 79% of theory. The colorless crystals melted at 73°–74°C after recrystallizing twice from cyclohexane.

EXAMPLE 28

(E)-4-(2'-Fluoro-4-biphenylyl)-3-butene-2-ol was prepared analogous to Example 25 from (E)-4-(2'-fluoro-4-biphenylyl)-3-butene-2-one with a yield of 77% of theory. After column-chromatographic purification on silicagel, using benzene as the eluant, as well as recrystallization from diisopropyl ether and cyclohexane, each in the presence of charcoal, the colorless crystals melted at 98°–99°C.

EXAMPLE 29

4-(2'-Chloro-4-biphenylyl)-2-butanol was prepared analogous to Example 26 from 4-(2'-chloro-4-biphenylyl)-2-butanone with a yield of 33% of theory. The compound was obtained as a colorless, viscous oil after chromatography on silicagel and was characterized by IR-, UV-, H-NMR-spectra and elemental analysis.

$C_{16}H_{17}Cl\,O$ (260.8): Calculated: C — 73.70%; H — 6.57%; Cl — 13.60%. Found: C — 73.60%; H — 6.71%; Cl — 13.73%.

EXAMPLE 30

(E)-4-(2'-Chloro-4-biphenylyl)-3-butene-2-ol was prepared analogous to Example 25 from (E)-4-(2'-chloro-4-biphenylyl)-3-butene-2-one with a yield of 95% of theory. The colorless crystals melted at 64°–65°C after recrystallization from diisopropyl ether/petroleum ether (ratio by volume 1:2) and cyclohexane.

EXAMPLE 31

(E)-4-(2-Fluoro-4-biphenylyl)-3-butene-2-ol was prepared analogous to Example 26 from (E)-4-(2-fluoro-4-biphenylyl)-3-butene-2-one with a yield of 88% of theory. The colorless crystals melted at 107°–108°C after three recrystallizations from cyclohexane.

EXAMPLE 32

4-(2-Chloro-4-biphenylyl)-2-butanol was prepared analogous to Example 26 from 4-(2-chloro-4-biphenylyl)-2-butanone with a yield of 78% of theory. The product was obtained as a colorless, viscous, non-crystallizing oil after chromatography on silicagel ($R_f$-value 0.60, prepared silicagel plates, thickness of layer 0.25 mm; benzene/ethyl acetate, ratio by volume 1:1, as eluant), which was characterized by IR-, UV-, NMR-spectra and by elementary analysis.

$C_{16}H_{17}Cl\,O$ (260.8): Calculated: C — 73.70%; H — 6.57%; Cl — 13.60%. Found: C — 73.50%; H — 6.74%; Cl — 13.38%.

EXAMPLE 33

(E)-4-(2-Fluoro-4-biphenylyl)-3-pentene-2-ol was prepared analogous to Example 25 from (E)-4-(2-fluoro-4-biphenylyl)-3-pentene-2-one with a yield of 88% of theory. The colorless crystals melted at 98°C after recrystallization from diisopropyl ether.

EXAMPLE 34

4-(2'-Chloro-4-biphenylyl)-2-pentanol was prepared analogous to Example 26 from 4-(2'-chloro-4-biphenylyl)-2-pentanone with a yield of 93% of theory. The colorless, viscous, non-crystallizing oil, consisting of a mixture of both possible diastereomers, was purified by distillation in a moderate vacuum: b.p. 126°–128°C. at 0.04 mm Hg.

$C_{17}H_{19}Cl\,O$ (274.8) Calculated: C — 74.31%; H — 6.97%; Cl — 12.90%. Found: C — 74.40%; H — 7.06%; Cl — 12.70%.

EXAMPLE 35

4-(2'-Fluoro-4-biphenylyl)-2-pentanol was prepared analogous to Example 26 from 4-(2'-fluoro-4-biphenylyl)-2-pentanone with a yield of 83% of theory. The colorless, viscous oil, consisting of a mixture of both possible diastereomers, had a b.p. of 122°–124°C at 0.06 mm Hg.

EXAMPLE 36

(E)-4-(2'-Fluoro-4-biphenylyl)-3-pentene-2-ol was prepared analogous to Example 26 from (E)-4-(2'-biphenylyl)-3-pentene-2-one with a yield of 73% of theory. The colorless crystals melted at 86°C recrystallization from cyclohexane.

EXAMPLE 37

(E)-4-(4-Biphenylyl)-3-pentene-2-ol was prepared analogous to Example 26 from (E)-4-(4-biphenylyl)-3-pentene-2-one with a yield of 66% of theory. The colorless crystals melted at 147° to 148°C after recrystallization from diisopropyl ether.

EXAMPLE 38

(E)-4-(2'-Chloro-4-biphenylyl)-3-pentene-2-ol was prepared analogous to Example 26 from (E)-4-(2'-chloro-4-biphenylyl)-3-pentene-2-one with a yield of 45% of theory. The colorless, non-crystallizing oil had a b.p. of 148°–150°C at 0.6 mm Hg.

EXAMPLE 39

4-(4-Biphenylyl)-2-pentanol was prepared analogous to Example 26 from 4-(4-biphenylyl)-2-pentanone with a yield of 88% of theory. The colorless crystals melted at 58°–60°C (cyclohexane). Only one of the possible diastereomers was present according to H-NMR-spectroscopic analysis.

EXAMPLE 40

4-(2'-Fluoro-4-biphenylyl)-2-butanone by method D 25.0 Gm (0.104 mol) of (E)-4-(2'-fluoro-4-biphenylyl)-3-butene-2-one, dissolved in 1500 ml of ethyl acetate, were hydrogenated at room temperature at a hydrogen pressure of 3 atmospheres and in the presence of 10 gm of Raney-nickel, until the rate of hydrogen absorption had clearly slowed down. The catalyst was filtered off, the filtrate was evaporated in vacuo, and the residue, consisting of a mixture of 4-(2'-fluoro-4-biphenylyl)-2-butanol and the desired 4-(2'-fluoro-4-biphenylyl)-2-butanone, was dissolved in a mixture of 155 ml of anhydrous dimethyl sulfoxide, 155 ml of dry benzene, 8.25 ml (0.102 mol) of pyridine and 4.15 ml (0.056 mol) of trifluoroacetic acid. After addition of 64.0 gm (0.31 mol) of N,N'-dicyclohexyl-carbodiimide the mixture was stirred at room temperature for 12 hours. Then the mixture was diluted with 2.5 liters of ether, and afterwards a solution of 39.08 gm (0.31 mol) of oxalic acid dihydrate in 250 ml of methanol was added dropwise while stirring. After the gas evolution lasting about 30 minutes was finished, 2.5 liters of water were added, and the insoluble N,N'-dicyclohexyl-urea was removed by filtration. The layers were separated, the organic layer was extracted twice with aqueous 5% sodium bicarbonate solution and once with water, dried over sodium sulfate, filtered, and the solvent was evaporated. The oily residue, still containing small quantities of dicyclohexyl-urea, was purified by chromatography on silicagel; using benzene as the eluant, and distilled twice in a moderate vacuum. 12.5 Gm (50% of theory) of the above mentioned ketone, b.p. 153°–155°C at 0.4 mm Hg, or b.p. 148°–150°C at 0.25 mm Hg and m.p. 30°C (petroleum ether), were obtained.

EXAMPLE 41

6-(4-Biphenylyl)-2-hexanone

A mixture of 6-(4-biphenylyl)-2-hexanone and 6-(4-biphenylyl)-2-hexanol, obtained by the Grignard reaction described in Example 12, was oxidized with dimethyl sulfoxide in the presence of N,N'-dicyclohexyl carbodiimide and pyridinium trifluoroacetate analogous to Example 40. The desired 6-(4-biphenylyl)-2-hexanone was obtained with a yield of 40% of theory. The colorless crystals melted at 51°–52°C (from petroleum ether).

EXAMPLE 42

6-(2'-Fluoro-4-biphenylyl)-2-hexanone by method D 20.0 Gm (0.0734 mol) of 6-(2'-fluoro-4-biphenylyl)-2-hexanol were dissolved in a mixture consisting of 110 ml of anhydrous dimethyl sulfoxide, 110 ml of absolute benzene, 5.9 ml (0.0732 mol) of pyridine and 2.95 ml (0.0397 mol) of trifluoroacetic acid. 45.5 Gm (0.22 mol) of N,N'-dicyclohexylcarbodiimide were added to the solution, and the mixture was stirred at room temperature for 14 hours. Then, the mixture was diluted with 2 liters of dry ether, a solution of 27.7 gm (0.22 mol) of oxalic acid dihydrate in 180 ml of methanol was added dropwise while stirring, and 2 liters of water were added after the gas evolution, lasting about 30 minutes, was compete. The insoluble N,N'-dicyclohexyl-urea was filtered off, and the aqueous and organic layers were separated. The organic layer was washed twice with aqueous 5% sodium bicarbonate solution and once with water, dried over sodium sulfate and evaporated. The residue was purified by chromatography on silicagel, using benzene as the eluant, and was subsequently recrystallized three times from petroleum ether. Yield: 7.0 gm (35% of theory) of colorless crystals, m.p. 37°–38°C.

EXAMPLE 43

8-(2'-Fluoro-4-diphenylyl)-2-octanone was prepared analogous to Example 42 from 8-(2'-fluoro-4-biphenylyl)-2-octanol by oxidation with dimethyl sulfoxide in the presence of pyridinium trifluoroacetate and N,N'-dicyclohexyl-carbodiimide with a yield of 80% of theory. The colorless crystals melted at 32°C after column-chromatographic purification on silicagel, using benzene/petroleum ether (ratio by volume = 9:1) as the eluant, and recrystallization from gasoline petroleum ether (ratio by volume = 1:1).

EXAMPLE 44

4-(2'-Chloro-4-biphenylyl)-2-butanone was prepared analogous to Example 42 from 4-(2'-chloro-4-biphenylyl)-2-butanol by oxidation with dimethyl sulfoxide in the presence of pyridinium trifluoroacetate and N,N'-dicyclohexyl-carbodiimide with a yield of 92% of theory. The colorless crystals melted at 34°–35°C after column-chromatographic purification on silicagel, using benzene/petroleum ether (ratio by volume = 2:1) as eluant, and recrystallization from petroleum ether and ethanol.

EXAMPLE 45

Using a procedure analogous to that described in Example 8, 82.5% of theory of 4-(4-biphenylyl)-2-pentanone, m.p. 59°–60°C, was obtained from 3-(4-biphenylyl)-butyramide and methyl magnesium iodide.

EXAMPLE 46

(E)-4-(2-Chloro-4-biphenylyl)-3-pentene-2-one by method F 208.0 Gm (1.85 mols) of potassium tert.-butylate were added all at once to a solution of 284.0 gm (1.23 mols) of 4-acetyl-2-chloro-biphenyl and 292.0 gm (1.85 mols) of ethyl (E)-3-ethoxy-crotonate in 1.8 liters of anhydrous dimethylformamide. The temperature rose at once from +20°C to +38°C, and the mixture turned red. The mixture was stirred for 1 hour at 32° to 35°C, then 200 ml of concentrated hydrochloric acid were added dropwise to the warm batch, and the resulting mixture was heated at a temperature of 90°–100°C for 30 minutes. After the carbon dioxide evolution had ceased, the cooled mixture was poured into 2 liters of ice water and extracted exhaustively with ether. The combined ether extracts were washed with water, with a saturated aqueous sodium bicarbonate solution and again with water, dried over sodium sulfate and evaporated. The oily residue was distilled in a moderate vacuum (b.p. 170°–175° C at 0.3 mm Hg) and subsequently recrystallized from cyclohexane and petroleum ether. 273.6 Gm (82% of theory) of pale yellow crystals, m.p. 66°–67°C, were obtained.

EXAMPLE 47

(E)-4-(2-Chloro-4-biphenylyl)-3-pentene-2-ol 80.0 Gm (0.296 mol) of (E)-4-(2-chlorobiphenylyl)-3-pentene-2-one were gently refluxed with 68.0 gm (0.333 mol) of aluminum isopropylate and 300 ml (3.92 mols) of isopropanol in a dry distillation apparatus with a 60-cm-Vigreux-column, such that only about 5 drops were distilled off per minute. After about 5 hours no acetone was found to be present in the distillate (using hydrochloric acid 2,4-dinitrophenyl-hydrazine solution) and in the reaction mixture no unreacted starting material could be found (by thin-layer-chromatography). The isopropanol was distilled off in a weak vacuum. The residue was hydrolyzed by addition of 300 gm of crushed ice. The ethereal (upper) phase, was decanted, and the aluminum hydrozide slurry was carefully washed with ether several times. The combined extracts were washed with water, with aqueous 5% sodium hydroxide and again with water, and dried over sodium sulfate. The solvent was evaporated in vacuo and the residue was recrystallized once from petroleum ether/ethyl acetate (ratio by volume = 4:1). Yield: 64.0 gm (79% of theory) of colorless crystals, m.p. 86°C.

EXAMPLE 48

4-(2-Chloro-4-biphenylyl)-2-pentanone by method B 17.3 Gm (0.0695 mol) of nickel(II)acetate tetrahydrate, dissolved in 600 ml of 95% ethanol, were reduced in a hydrogenation apparatus in a hydrogen atmosphere with 70 ml of a 1 M sodium borohydride solution to black, colloidal nickel boride (P-2-catalyst). To remove any unreacted borohydride which may be present, 16 gm (0.276 mol) of acetone were first added, and then the mixture was shaken at room temperature for 1 hour and, after addition of 35.0 gm (0.129 mol) of (E)-4-(2-chloro-4-biphenylyl)-3-pentene-2-one, hydrogenated at a hydrogen pressure of 5 atmospheres until hydrogen absorption had ceased. The catalyst was filtered off, the filtrate was evaporated in vacuo, and the residue was distributed between the water and ethyl acetate. The organic layer was dried over sodium sulfate and evaporated, and the residue was distilled in a high vacuum. 28.0 Gm (80% of theory) of colorless crystals were obtained which, after recrystallization from methanol, melted 54°–55°C.

EXAMPLE 49

4-(2-Chloro-4-biphenylyl)-2-pentanol by method B 40.0 Gm (0.147 mol) of (E)-4-(2-chloro-4-biphenylyl)-3-pentene-2-ol, dissolved in 800 ml of ethyl acetate, were hydrogenated at room temperature and at a hydrogen pressure of 3 atmospheres in the presence of 15.0 gm of Raney-nickel until hydrogen absorption had ceased. The catalyst was then filtered off, and the filtrate was evaporated in vacuo. The residue, a colorless, non-crystallizing, highly viscous oil, was purified by chromatography on silicagel, first using benzene and then benzene/ethyl acetate (ratio by volume = 9:1) as the eluant. The product, a mixture of both possible diastereomers, was not stable enough for distillation in a high vacuum. The characterization was effected by IR-, UV- and H-NMR-spectra as well as by elemental analysis:

$C_{17}H_{19}Cl\ O$ (274.8): Calculated: C — 74.31%; H — 6.97%; Cl — 12.90%. Found: C — 74.70%, H — 7.17%; Cl — 12.75%. Yield: 35.0 gm (87% of theory).

EXAMPLE 50

(E)-4-(2-Chloro-4-biphenylyl)-3-butene-2-ol by method C 30.0 Gm (0.117 mol) of (E)-4-(2-chloro-4-biphenylyl)-3-butene-2-one, dissolved in 150 ml of 95% ethanol, were added in small amounts within 10 minutes to a solution of 2.7 gm (0.0714 mol) of sodium borohydride in 200 ml of 95% ethanol. Subsequently the mixture was stirred for 1 hour at room temperature. The excess reducing agent was removed by careful addition of 4 gm of glacial acetic acid. The solvent was then distilled off in a water aspirator vacuum. 500 ml of water were added to the residue, and the mixture was exhaustively extracted with ether. The combined ether extracts were washed with water, dried over sodium sulfate and evaporated. The residue, a colorless viscous oil, was distilled in a high vacuum, b.p. 175°–180°C at 0.1 mm Hg. Yield: 23.0 gm (76% of theory).

$C_{16}H_{15}Cl\ O$ (258.75): Calculated: C — 74.27%; H — 5.84%; Cl — 13.70%. Found: C — 73.90%; H — 5.95%; Cl — 13.72%.

EXAMPLE 51

(E)-4-(3-Chloro-4-cyclohexyl-phenyl)-3-butene-2-one by method E 222.72 Gm (1.0 mol) of 3-chloro-4-cyclohexyl-benzaldehyde, 3,500 gm (60.3 mols) of acetone and 200 ml of methanol were charged into a 6-liter three-necked flask equipped with a stirrer, dropping funnel and internal thermometer. While thoroughly stirring the contents of the flask, a solution of 2.805 gm (0.05 mol) of potassium hydroxide in 16 ml of water was added dropwise thereto, while an internal temperature of 20° to 25°C was maintained. The mixture was then stirred for 3 hours more. The precipitate solid by-product was filtered off, and the filtrate was neutralized by dropwise addition of glacial acetic acid, and concentrated by evaporation in vacuo. The residue was shaken with a mixture of water and ether. The ether phase separated, dried over sodium sulfate, clarified with charcoal, and evaporated. The residual oil was distilled in a high vacuum (b.p. 162°–175°C at 0.2 mm Hg), crystallized by trituration with a small quantity methanol, and finally recrystallized once from methanol. The colorless crystals melted at 48°–49°C. Yield: 40 % of theory.

EXAMPLE 52

(E)-4-(3-Chloro-4-cyclohexyl-phenyl)-3-pentene-2-one by method F 87.6 Gm (0.781 mol) of potassium-tert.butylate were added all at once to a solution of 185.0 gm (0.781 mol) of 3'-chloro-4'-cyclohexyl-acetophenone and 123.0 gm (0.777 mol) of ethyl (E)-3-ethoxy-crotonate in 1.1 liters of anhydrous dimethyl formamide, whereby the temperature rose spontaneously from +20° to +38°C and the mixture turned deep red. The mixture was stirred for another hour with the temperature being maintained at 32°–35°C, and then 200 ml of concentrated hydrochloric acid added dropwise to the still warm mixture, and the resulting mixture was heated for 60 minutes at a temperature of 90°–100°C. After carbon dioxide evolution had ceased, the cooled mixture was stirred into 1 liter of ice water, and the aqueous mixture was exhaustively extracted with ether. The combined ether extracts were washed with water, dried over sodium sulfate and concentrated by evaporation. The residue was distilled in a vacuum (b.p. 175°–183°C at 0.1 mm Hg) and subsequently recrystallized twice from methanol, in the presence of activated charcoal. The colorless crystals, m.p. 56.5°–57.5°C were obtained with a yield of 132 gm (61% of theory).

EXAMPLE 53

(E)-4-(4-cyclohexyl-phenyl)-3-pentene-2-one was prepared analogous to Example 52 from 4'-cyclohexyl-acetophenone and ethyl (E)-3-ethoxy-crotonate with a yield of 55% of theory. B.p. 148°–151°C at 0.4 mm Hg; m.p. 49°–50°C (after recrystallization from methanol and petroleum ether). Characteristic signals in NMR (CDCl$_3$): $\tau$ 3.50 (1H-$q$; /J/=1.2 ± 0.1 Hz); $\tau$ 7.50 (3H-$d$; /J/=1.2 ± 0.1 Hz).

EXAMPLE 54

(E)-4-(3-Bromo-4-cyclohexyl-phenyl)-3-pentene-2-one was prepared analogous to Example 52, from 3'-bromo-4'-cyclohexylacetophenone (b.p. 135°–138°C at 0.15 mm Hg; $n_D^{20}$ = 1.5740) an ethyl (E)-3-ethoxy-crotonate with a yield of 69% of theory. B.p. 170°–175°C at 0.3 mm Hg; m.p. 52°–53°C (from methanol).

EXAMPLE 55

(E,E)-4-[4-(2-methyl-cyclohexyl)-phenyl]-3-pentene-2-one was prepared analogous to Example 52 from trans-4'-(2-methylcyclohexyl)-acetophenone (b.p. 115°–120°C at 0.1 mm Hg; $n_D^{20}$ = 1.5388) and ethyl (E)-3-ethoxy-crotonate with a yield of 61% of theory. B.p. 149°–151°C at 0.1 mm Hg; m.p. 34°–35°C (from methanol).

EXAMPLE 56

(E)-4-(4-cyclohexyl-phenyl)-3-hexene-2-one was prepared analogous to Example 52 from 4'-cyclohexyl-propiophenone and ethyl (E)-3-ethoxy-crotonate with a yield of 18% of theory [after column-chromatographic purification on silicagel, using first petroleum ether, then petroleum ether/benzene (volumetric ratio 3:1), and finally benzene as the eluant]. Complete separation of the isomeric unsaturated ketones, in particular the two geometric isomers of 4-(4-cyclohexyl-phenyl)-4-hexene-2-one, was not possible. B.p. 168°–175°C at 0.6 mm Hg.

EXAMPLE 57

(E)-4-(4-isobutyl-phenyl)-3-pentene-2-one was prepared analogous to Example 52 from 4'-isobutyl-acetophenone 1st ethyl 3rd 3-ethoxy-crotonate with the yield of example, % of theory. B.p. 115°–125°C at 0.2 mm Hg.

EXAMPLE 58 toluene, continuously the alcoholate isopropylate, (E)-4-(3-chloro-4-isobutyl-phenyl)-3-pentene-2-one was prepared analogous to Example 52 from 3'-chloro-4'-isobutyl-acetophenone (b.p. 89°–93°C at 0.2 mm Hg) and ethyl (E)-3-ethoxy-crotonate with a yield of 61% of theory (after chromatographic purification on silicagel using petroleum-ether/benzene in a volume ratio of 1:1 as eluant). Colorless oil.

$C_{15}H_{19}Cl\ O$ (250.8): Calculated: C — 71.84%; H — 7.64%; Cl — 14.14%. Found: C — 72.30%; H — 7.68%; Cl — 13.85%.

EXAMPLE 59

(E)-4-(4-cycloheptyl-phenyl)-3-pentene-2-one was prepared analogous to Example 52 from 4'-cycloheptyl-acetophenone (b.p. 120°–125°C at 0.03 mm Hg) and methyl (E)-3-methoxy-crotonate with a yield of 28% of theory. B.p. 132°–135°C at 0.1 mm Hg.

EXAMPLE 60

(E)-4-(3-chloro-4-cycloheptyl-phenyl)-3-pentene-2-one was prepared analogous to Example 52 from 3'-chloro-4'-cycloheptyl-acetophenone (b.p. 136°–139°C at 0.1 mm Hg; $n_D^{23} = 1.5572$) and ethyl (E)-3-ethoxy-crotonate with a yield of 51% of theory. B.p. 160°–165°C at 0.1 mm Hg.

EXAMPLE 61

4-(4-Cyclohexyl-phenyl)-2-pentanone by method A

A solution of 24.54 gm (0.1 mol) of 3-(4-cyclohexyl-phenyl)-butyramide in 750 ml of dry methylene chloride was added dropwise within one hour to a methyl magnesium iodide solution, prepared from 12.2 gm (0.5 mol) of magnesium and 71 gm (0.5 mol) of methyl iodide in a total of 400 ml of anhydrous ether, and, to complete the reaction, the resulting mixture was refluxed for 6 hours. The cooled mixture was then stirred into a mixture of 2 kg of ice and 100 ml of concentrated sulfuric acid. The organic phase was separated and washed twice with water, then with a saturated aqueous sodium bicarbonate solution and finally once more with water, then dried over anhydrous magnesium sulfate and concentrated by evaporation in vacuo. The residue was chroomatographically purified on 800 gm of silicagel, using benzene as the eluant, and the evaporated eluates were finally distilled in vacuo. 19.8 gm (81% of theory) of colorless oil, b.p. 104°–106°C at 0.05 mm Hg were obtained.

EXAMPLE 62

4-(3-Chloro-4-cyclohexyl-phenyl)-2-pentanone was prepared analogous to Example 61 from 3-(3-chloro-4-cyclohexyl-phenyl)-butyramide and methyl-magnesium bromide with a yield of 74% of theory. The colorless, highly viscous oil had a b.p. of 153°–156°C at 0.1 mm Hg.

EXAMPLE 63

4-(3-Chloro-4-cyclohexyl-phenyl)-2-butanol by method A

A Grignard reagent was prepared, under exclusion of atmospheric oxygen, from 50.68 gm (0.168 mol) of 1-bromo-2-(3-chloro-4-cyclohexyl-phenyl)-ethane and 4.0 gm (0.165 mol) of magnesium in 60 ml of anhydrous ether, and to this reagent a solution of 7.23 gm (0.165 mol) of acetaldehyde in 10 ml of dry ether was added dropwise, while stirring. All of these operations were carried out in an atmosphere of pure nitrogen. The resulting mixture was heated, while stirring, for 2 hours on a water bath. It was then cooled, hydrolyzed by adding 50 gm of crushed ice, and subsequently sufficient 50% hydrochloric acid was added to dissolve the initially formed precipitate completely. The ehtereal layer was separated. The aqueous phase was extracted twice with ether, and the combined ethereal extracts were washed with water, with a saturated aqueous sodium bicarbonate solution, and once more with water. After drying over sodium sulfate, the ether was distilled off, and the residue was distilled in vacuo. 24.3 gm (55% of theory) of a colorless oil, b.p. 167°–175°C at 0,05 mm Hg were obtained.

EXAMPLE 64

4-(4-Cyclohexyl-phenyl)-2-pentanol by method A

Analogous to Example 63, the Grignard reagent prepared from 33.19 gm (0.118 mol) of 1-bromo-2-(4-cyclohexylphenyl)-propane and 2.9 gm (0.119 mol) of magnesium was reacted with 8.15 gm (0.185 mol) of acetaldehyde in absolute ether. The resulting mixture of 4-(4-cyclohexyl-phenyl)-2-pentanol and 4-(4-cyclohexyl-phenyl)-2-pentanone (28 gm; about 96% of theory) was dissolved in 1 liter of ethanol and, after addition of a solution of 2.10 gm (0.056 mol) of sodium borohydride in 300 ml of ethanol, the mixture was stirred for one hour at room temperature. The excess sodium borohydride was decomposed by addition of 3 ml of glacial acetic acid. The mixture was subsequently evaporated, and the residue was taken up in 500 ml of water and then exhaustively extracted with ether. The combined ether exracts were dried over sodium sulfate, evaporated and the residue was distilled at its b.p. of 113°–115°C at 0.08 mm Hg. Yield: 21.7 gm (75% of theory). According to NMR-spectra, a mixture of the two possible diastereomers was present.

$C_{17}H_{26}O$ (246.4): Calculated: C — 82.87%; H — 10.64%. Found: C — 82.70%; H — 10.78%.

EXAMPLE 65

4-(3-Chloro-4-cyclohexyl-phenyl)-2-pentanol was prepared analogous to Example 64 from a Grignard reagent, prepared from 91.55 gm (0.29 mol) of 1-bromo-2-(3-chloro-4-cyclohexyl-phenyl)-propane and 7.08 gm (0.291 mol) of magnesium, and 14.2 gm (0.32 mol) of acetaldehyde, followed by reduction with sodium borohydride. The above compound was obtained as a mixture of the two possible pairs of diastereomeric isomers. The colorless oil (39.5 gm; 48% of theory) was not sufficiently heat-stable for distillation, and therefore had to be chromatographically purified (silicagel; benzene as the eluant).

$C_{17}H_{25}Cl\,O$ (280.85): Calculated: C — 72.71%; H — 8.96%; Cl — 12.63%. Found: C — 72.90%; H — 9.08%; Cl — 12.25%.

EXAMPLE 66

4-(3-Chloro-4-cyclohexyl-phenyl)-2-butanone by method B

In a hydrogenation apparatus 15 gm (0.06 mol) of nickel(II)acetate tetrahydrate, dissolved in 600 ml of 95% ethanol, were reduced in an atmosphere of hydrogen with 60 ml of a 1 M sodium borohydride solution, to yield black colloidal nickel boride (P-2-catalyst). In order to remove any unreacted borohydride, 14 gm (0.24 mol) of acetone were added, and the resulting mixture was shaken for 1 hour at room temperature and, after addition of 32.32 gm (0.123 mol) of (E)-4-(3-chloro-4-cyclohexyl-phenyl)-3-butene-2-one, it was hydrogenated at 5 atmospheres of hydrogen pressure until hydrogen absorption has ceased. The catalyst was filtered off, and the filtrate was concentrated by evaporation in vacuo. The residue shaken with a mixture of water and ethyl acetate, the organic phase was isolated, dried over sodium sulfate and evaporated, and the residue was distilled in vacuo. 19.0 Gm (58% of theory) of a colorless, viscous oil, b.p. 140°–148°C at 0.03 mm Hg were obtained.

$C_{16}H_{21}Cl\,O$ (264.8): Calculated: C — 72.57%; H — 7.98%; Cl — 13.39%. Found: C — 72.70%; H — 8.04%; Cl — 13.25%.

EXAMPLE 67

4-(3-Bromo-4-cyclohexyl-phenyl)-2-pentanol was prepared analogous to Example 66 from (E)-4-(3-bromo-4-cyclohexyl-phenyl)-3-pentene-2-ol with a yield of 83% of theory. A mixture of the two diastereomers was obtained as a colorless, viscous oil, b.p. 147°–153°C at 0.06 mm Hg.

$C_{17}H_{25}Br\,O$ (325.3): Calculated: C — 69.77%; H — 7.75%; Br — 24.57%. Found: C — 63.20%; H — 8.04%; Br — 24.40%.

EXAMPLE 68

4-(3-Bromo-4-cyclohexyl-phenyl)-2-pentanone was prepared analogous to Example 66 from (E)-4-(3-bromo-4-cyclohexylphenyl)-3-pentene-2-one with a yield of 92% of theory (after column-chromatographic purification on silicagel, using benzene as the eluant).

$C_{17}H_{23}Br\,O$ (323.3): Calculated: C — 63.16%; H — 7.17%; Br — 24.72%. Found: C — 63.60%; H — 7.03%; Br — 24.70%.

EXAMPLE 69

(E)-4-[4-(2-methyl-cyclohexyl)-phenyl]-2-pentanone was prepared analogous to Example 66 from (E,E)-4-[4-(2-methyl-cyclohexyl)-phenyl]-3-pentene-2-one, with a yield of 93% of theory. B.p. 148°–153°C at 0.07 mm Hg.

$C_{18}H_{26}O$ (258.4):
Calculated: C — 83.67%; H — 10.14%. Found: C — 83.30%; H — 10.40%.

EXAMPLE 70

4-(4-Cyclohexyl-phenyl)-2-hexanone was prepared analogous to Example 66 from the mixture of isomers of 4-(4-cyclohexylphenyl)-3-hexene-2-one and 4-(4-cyclohexyl-phenyl)-3-hexene-2-one and 4-(4-cyclohexyl-phenyl)-4-hexene-2-one obtained in Example 56. Yield: 86% of theory. B.p. 137°–142°C at 0.1 mm Hg.

$C_{18}H_{26}O$ (258.4): Calculated: C — 83.67%; H — 10.14%. Found: C — 83.60%; H — 10.22%.

EXAMPLE 71

(E)-4-(3-Chloro-4-cyclohexyl-phenyl)-3-butene-2-ol

In a dry distillation apparatus with a 60-cm Vigreux-column, a mixture of 15.37 gm (0.0585 mol) of (E)-4-(3-chloro-4-cyclohexyl-phenyl)-3-butene-2-one, 12.5 gm (0.0612 mol) of aluminum isopropylate and 190 ml (2.48 mols) of isopropanol was gently refluxed so that only about 5 drops per minute distilled over. After about 5 hours no acetone could be detected in the distillate (with a hydrochloric acid 2,4-dinitrophenolhydrazine solution), nor could any starting substance be detected in the reaction mixture (by thin-layer chromatography). The isopropanol was distilled off in weak vacuum. The residue was hydrolyzed by the addition of 50 gm of crushed ice and 34 ml of 6 N hydrochloric acid. Exhaustive extraction with ethyl acetate was performed, and the combined organic extracts were washed with water, with an aqueous 5% sodium hydroxide solution and once more with water, and then dried over sodium sulfate. The solvent was evaporated in vacuo, the residue was taken up in petroleum ether, the solution was treated with activated charcoal and concentrated by evaporation once more. The product obtained with a yield of 13.32 gm (86% of theory) was a colorless, viscous, strongly refractive oil, which, according to IR-, UV- and NMR-spectra was (E)-4-(3-chloro-4-cyclohexyl-phenyl)-3-butene-2-ol.

$C_{16}H_{21}Cl\,O$ (264.8): Calculated: C — 72.57%; H — 7.99%; Cl — 13.39%. Found: C — 72.70%; H — 8.05%; Cl — 13.25%.

EXAMPLE 72

(E)-4-(3-Chloro-4-cyclohexyl-phenyl)-3-pentene-2-ol was prepared analogous to Example 71 from (E)-4-(3-chloro-4-cyclohexyl-phenyl)-3-pentene-2-one with a yield of 68% of theory (after columnn-chromatographic purification on silicagel, using benzene as the eluant; and then on activated charcoal, using first petroleum ether then acetone, and finally ethyl acetate as the eluants). The compound could not be distilled without decomposition. The colorless, highly viscous oil also showed no tendency to crystallize.

$C_{17}H_{23}Cl\,O$ (278.8): Calculated: C — 73.23%; H — 8.31%; Cl — 12.72%. Found: C — 73.40%; H — 8.42%; Cl — 12.85%.

Characteristic signals in NMR (CDCl$_3$); $\tau$ 4.23 (1H, AB$_3$X — Type, $/J/ = 8.4 \pm 0.1$ Hz and $/J/ = 1.3 \pm 0.1$ Hz), $\tau$ 7.99 (3H-$d$; $/J/ = 1.3 \pm 0.1$ Hz).

EXAMPLE 73

(E)-4-(4-Cyclohexyl-phenyl)-3-pentene-2-ol was prepared analogous to Example 71 from (E)-4-(4-cyclohexyl-phenyl)-3-pentene-2-one, in a yield of 74% of theory. M.p. 67.5°–68.0°C (after two recrystallizations from petroleum ether in the presence of activated charcoal).

$C_{17}H_{24}O$ (244.4): Calculated: C — 83.55%; H — 9.90%. Found: C — 83.70%; H — 9.88%.

EXAMPLE 74

(E)-4-(3-Bromo-4-cyclohexyl-phenyl)-3-pentene-2-ol was prepared analogously to Example 71 from (E)-4-(3-bromo-4-cyclohexyl-phenyl)-3-pentene-2-one. The substance was obtained as a colorless oil with a yield of 91% of theory after chromatographic purification, using benzene as eluant.

$C_{17}H_{23}BrO$ (323.3): Calculated: C — 63.16%; H — 7.17%; Br — 24.72%. Found: C — 63.70%; H — 7.40%; Br — 24.00%.

Characteristic signals in NMR (CDCl$_3$); $\tau$ 4.22 (1H, AB$_3$X-Type), $\tau$ 8.00 (3H-$d$).

EXAMPLE 75

(E)-4-[4-(2-Methyl-cyclohexyl)-phenyl]-2-pentanol was prepared analogously to Example 67 from (E)-4-[4-(2-methyl-cyclohexyl)-phenyl]-2-pentanone with a yield of 76% of theory. The colorless viscous oil, b.p. 146°–149°C at 0.1 mm Hg was obtained as a mixture of the two pairs of diastereoisomers.

$C_{18}H_{28}O$ (260.4): Calculated: C — 83.02%; H — 10.84%. Found: C — 82.80%; H — 10.80%.

EXAMPLE 76

4-(4-Cyclohexyl-phenyl)-2-hexanol was prepared analogous to Example 29 from 4-(4-cyclohexyl-phenyl)-2-hexanone with a yield of 90% of theory. The colorless, viscous oil, a mixture of the two possible diastereomers, had a b.p. 142°–148°C at 0.07 mm Hg.

$C_{18}H_{28}O$ (260.2): Calculated: C — 83.02%; H — 10.84%. Found: C — 82.70%; H — 10.78%.

EXAMPLE 77

(E)-4-(4-isobutyl-phenyl)-3-pentene-2-ol was prepared analogous to Example 71 from (E)-4-(4-isobutyl-phenyl)-3-pentene-2-one with a yield of 61% of theory. The colorless, viscous oil had a b.p. 98°–100°C at 0.02 mm Hg.

$C_{15}H_{22}O$ (218.3): Calculated: C — 82.52%; H — 10.16%. Found: C — 82.30%; H — 10.26%.

Characteristic signals in NMR (CDCl$_3$):$\tau$ 4.20 (1H, AB$_3$X-Type), $\tau$ 7.94 (3H-d)

EXAMPLE 78

(E)-4-(3-chloro-4-isobutyl-phenyl)-3-pentene-2-ol was prepared analogous to Example 71 from (E)-4-(3-chloro-4-isobutyl-phenyl)-3-pentene-2-one with a yield of 42% of theory. B.p. 100°–105°C at 0.02 mm Hg.

$C_{15}H_{21}ClO$ (252.8): Calculated: C — 71.27%; H — 8.37%; Cl — 14.02%. Found: C — 71.60%; H — 8.66%; Cl — 13.85%.

Characteristic signals in NMR (CDCl$_3$):$\tau$ 4.17 (1H, AB$_3$X-Type), $\tau$ 8.02 (3H-$d$).

EXAMPLE 79

(E)-4-(4-cycloheptyl-phenyl)-3-pentene-2-ol was prepared analogous to Example 71 from (E)-4-(3-chloro-4-cycloheptyl-phenyl)-3-pentene-2-one with a yield of 18% of theory. M.p. 64°–65°C (from petroleum ether).

$C_{18}H_{26}O$ (258.4): Calculated: C — 83.67%; H — 10.14%. Found: C — 83.80%; H — 10.13%.

Characteristic signals in NMR (CDCl$_3$):$\tau$ 4.21 (1H, AB$_3$X-Type), $\tau$ 7.94 (3H-$d$)

EXAMPLE 80

(E)-4-(4-cyclopentyl-phenyl)-3-pentene-2-one was prepared analogously to Example 52 from 4'-cyclopentyl-acetophenone and ethyl (E)-3-ethoxy-crotonate with a yield of 51% of theory. B.p. 143°–147°C at 0.05 mm Hg. M.p. 33°–33.5°C (from methanol).

EXAMPLE 81

4-(4-Cyclopentyl-phenyl)-2-pentanone was prepared analogous to Example 66 from (E)-4-(4-cyclopentyl-phenyl)-3-pentene-2-one with a yield of 72% of theory. B.p. 130°–140°C at 0.03 mm Hg.

$C_{16}H_{22}O$ (230.35): Calculated: C — 83.43%; H — 9.63%. Found: C — 83.50%; H — 9.71%.

EXAMPLE 82

(E)-4-(3-chloro-4-cyclopentyl-phenyl)-3-pentene-2-one was prepared analogous to Example 52 from 3'-chloro-4'-cyclopentyl-acetophenone (b.p. 130°–135°C at 0.1 mm Hg) and ethyl (E)-3-ethoxy-crotonate with a yield of 82% of theory. B.p. 130°–135°C at 0.1 mm Hg.

$C_{16}H_{19}ClO$ (262.8): Calculated: C — 73.13%; H — 7.29%; Cl — 13.49%. Found: C — 73.10%; H — 7.43%; Cl — 13.40%.

EXAMPLE 83

4-(3-Chloro-4-cyclopentyl-phenyl)-2-pentanone was prepared analogously to Example 66 from (E)-4-(3-chloro-4-cyclopentyl-phenyl)-3-pentene-2-one with a yield of 64% of theory. B.p. 135°–140°C at 0.1 mm Hg.

$C_{16}H_{21}ClO$ (264.8): Calculated: C — 72.58%; H — 7.99%; Cl — 13.39%. Found: C — 72.80%; H — 8.25%; Cl — 13.00%.

The compounds of the formula I above have useful pharmacodynamic properties. More particularly, they exhibit very effective antiphlogistic activities in warm-blooded animals, such as rats.

The antiphlogistic activity of the compounds of this invention was ascertained by the standard pharmacological test methods described below, and the tables show the test results obtained for a representative cross-section of compounds embraced by formula I, where:

A = (E)-4-(2-fluoro-4-biphenylyl)-3-butene-2-ol
B = 4-(2-fluoro-4-biphenylyl)-2-butanol
C = 8-(2'-fluoro-4-biphenylyl)-2-octanol
D = 6-(2'-fluoro-4-biphenylyl)-2-hexanone
E = 4-(4-biphenylyl)-2-pentanone
F = 8-(2'-fluoro-4-biphenylyl)-2-octanone
G = (E)-4-(4-biphenylyl)-3-pentene-2-one
H = (E)-4-(2'-fluoro-4-biphenylyl)-3-pentene-2-one
I = 4-(2-fluoro-4-biphenylyl)-2-pentanol
K = (E)-4-(2'-fluoro-4-biphenylyl)-3-pentene-2-ol
L = (E)-4-(2-chloro-4-biphenylyl)-3-pentene-2-one
M = (E)-4-(2-chloro-4-biphenylyl)-3-pentene-2-ol
N = 4-(2-chloro-4-biphenylyl)-2-pentanone
O = 4(2-chloro-4-biphenylyl)-2-pentanol
P = (E)-4-(3-chloro-4-cyclohexyl-phenyl)-3-pentene-2-one
Q = 4-(3-chloro-4-cyclohexyl-phenyl)-2-pentanone
R = (E)-4-(3-chloro-4-cyclohexyl-phenyl)-3-pentene-2-ol
S = 4-(3-chloro-4-cyclohexyl-phenyl)-2-pentanol
T = (E)-4-(4-cyclohexyl-phenyl)-3-pentene-2one U = 4-(4-cyclohexyl-phenyl)-2-pentanone
V = (E)-4-(4-cyclohexyl-phenyl)-3-pentene-2-ol
W = 4-(4-cyclohexyl-phenyl)-2-pentanol
X = (E)-4-(3-bromo-4-cyclohexyl-phenyl)-3-pentene-2-one
Y = 4-(3-bromo-4-cyclohexyl-phenyl)-2-pentanone
Z = (E)-4-(3-bromo-4-cyclohexyl-phenyl)-3-pentene-2-ol
AA = 4-(3-bromo-4-cyclohexyl-phenyl)-2-pentanol
BB = (E,E)-4-[4-(2-methyl-cyclohexyl)-phenyl]-3-pentene-2-one
CC = (E)-4-[4-(2-methyl-cyclohexyl)-phenyl]-2-pentanone
DD = (E)-4-(3-chloro-4-isobutyl-phenyl)-3-pentene-2-one
EE = (E)-4-(3-chloro-4-isobutyl-phenyl)-3-pentane-2-ol
FF = (E)-4-(4-cyclohexyl-phenyl)-3-pentene-2-ol The compunds were tested for their anti-exudative effect on Kaolin-induced edema and carrageenin-induced edema in the hind paw of the rat after oral administration to the rat.

a. Kaolin-induced edema of the hind paw of the rat

The kaolin edema was induced according to the method given by Hillebrecht [*Arzneimittel-Forsch.* 4, 607 (1954)] by subplanar injection of 0.05 ml of a 10% suspension of kaolin in a 0.85% sodium chloride solution. Measurement of the thickness of the paws was effected using the technique of Doepfner and Cerletti [*Int. Arch. Allergy Immunol.* 12, 89 (1958)].

The test compound was administered orally to male FW 49 rats weighing 120–150 gm by means of an esophageal tube 30 minutes before inducing the edema. 5 hours after inducing the edema the average size of the swelling in the rats treated with the test compound was compared with the size of the swelling in blind-treated control animals. By graphic extrapolation the dose leading to a 35% of the swelling ($ED_{35}$) was calculated from the percentage reduction in the size of the swelling caused by the administration of different doses.

b. Carrageenin-induced edema of the hind paw of the rat

The carrageenin edema was induced according to the method of Winder et al. [*Proc. Soc. exp. Biol. Med.* 111, 544 (1962)] by subplanar injection of 0.05 ml of a 1% solution of carrageenin in a 0.85% solution of sodium chloride. The test compound was administered 60 minutes before the provocation of the edema.

For the calculation of the reductive effect on the edema, the size of the swelling was measured 3 hours after the provocation of the edema. All other details were the same as described above in the case of the kaolin edema.

The results obtained in these tests are shown in the following table.

TABLE I

| Compound | Kaolin edema $ED_{35}$ per os mgm/kg | Carrageenin edema $ED_{35}$ per os mgm/kg | Average value $ED_{35}$ mgm/kg |
| --- | --- | --- | --- |
| A | 15 | 12.4 | 13.7 |
| B | 16 | 12.0 | 14.0 |
| C | 15 | 17 | 16 |
| D | 9 | 10.5 | 9.75 |
| E | 21 | 15 | 18 |
| F | 9.8 | 14.5 | 12.15 |
| G | 23.5 | 8.6 | 16.05 |
| H | 37 | 8.9 | 22.95 |
| I | 17 | 16.5 | 16.75 |

TABLE I-continued

| Compound | Kaolin edema $ED_{35}$ per os mgm/kg | Carrageenin edema $ED_{35}$ per os mgm/kg | Average value $ED_{35}$ mgm/kg |
| --- | --- | --- | --- |
| K | 17.5 | 12.8 | 15.15 |
| L | 15.5 | 5.6 | 10.55 |
| M | 26 | 23 | 24.5 |
| N | 31.5 | 16.5 | 24 |
| O | 48 | — | — |
| P | 17 | 8.6 | 12.8 |
| Q | 5.0 | 2.5 | 3.75 |
| R | 4.8 | 3.1 | 3.95 |
| S | 7.6 | 7.0 | 7.3 |
| T | 12.5 | 12.0 | 12.25 |
| U | 15 | — | — |
| V | 13.3 | 7.6 | 10.45 |
| W | 26 | — | — |
| X | 22 | 22 | 22 |
| Y | 13 | — | — |
| Z | 16 | — | — |
| AA | 28 | 18.5 | 23.25 |
| BB | 19 | 13 | 16 |
| CC | 29 | 21 | 25 |
| DD | 50 | 19 | 34.5 |
| EE | 54 | 52 | 53 |
| FF | 49 | 35 | 42 |

The adjuvant arthritis tests on rats were performed in analogy to the procedure described by Rosenthale and Nagra [*Proc. Soc. exp. Biol. Med.* 125, 149 (1967)].

Male FW 49-rats were given a subplantar injection of 0.1 ml of a 1% suspension of M.butyricum in viscous paraffin oil in a hind paw. The test compound was administered, beginning with the M.butyricum injection, once daily for 20 days by esophageal tube.

On the 21st day after inducing the arthritis, the volumes of the right paw (non-specific primary reaction at the place of injection) and the left paw (immunologically predicated specific secondary reaction) of the animals treated with the test compound were compared with those of the blind-treated control animals. From the swelling reduction obtained with the various doses, an $ED_{50}$ was graphically determined.

The results obtained in this test are shown in the following table.

TABLE II

| Compound | Kaolin edema $ED_{35}$ per os mgm/kg | Carrageenin edema $ED_{35}$ per os mgm/kg | Adjuvant arthritis-rat $ED_{50}$ per os | |
| --- | --- | --- | --- | --- |
| | | | Primary reaction mgm/kg | Secondary reaction mgm/kg |
| P | 17 | 8.6 | <0.7 | <0.60 |
| R | 4.8 | 3.1 | <0.3 | <0.70 |
| Q | 5.0 | 2.5 | <0.4 | <0.2 |
| E | 21 | 15 | <4.0 | <4.0 |
| K | 17.5 | 17 | <1.5 | <2.0 |
| H | 37 | 11 | <2.0 | <1.0 |

The above data show that, because of their preferential anti-arthritic activity, the compounds of this invention should have decisive advantages as therapeutics against primary chronic polyarthritis over non-specific-acting antiphlogistics.

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective antiphlogistic dosage unit of the compounds according to the present invention is from 0.083 to 6.7 mgm/kg body weight, preferably from 0.16 to 1.67 mgm/kg body weight. The daily dose rate is 0.33 to 16.7 mgm/kg, preferably 1.25 to 6.7 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 84

Tablets

The tablets composition is compounded from the following ingredients:

| | | |
|---|---|---|
| (E)-4-(2-Fluoro-4-biphenylyl)-3-butene-2-ol | 50.0 | parts |
| Corn starch | 247.0 | " |
| Polyvinylpyrrolidone | 10.0 | " |
| Magnesium stearate | 3.0 | " |
| Total | 310.0 | parts |

Preparation

A mixture of the active ingredient and the corn starch was moistened with an aqueous 14% solution of the polyvinylpyrrolidone and passed through a 1.5 mm-mesh screen. The granulate thus obtained was dried at 45°C and passed once more through the said screen. The dry granulate was admixed with magnesium stearate, and the composition was compressed into 310 mgm-tablets. Each tablet contained 50 mgm of the butanol compound and was an oral dosage unit composition with effective antiphlogistic action.

EXAMPLE 85

Coated pills

The pill core composition is compounded from the following ingredients:

| | | |
|---|---|---|
| (E)-4-(3-Chloro-4-cyclohexyl-phenyl)-3-pentene-2-one | 25.0 | parts |
| Corn starch | 245.0 | " |
| Gelatin | 8.0 | " |
| Talcum | 18.0 | " |
| Magnesium stearate | 4.0 | " |
| Total | 300.0 | parts |

Preparation

A mixture of the active ingredient and the corn starch was moistened and an aqueous 10% solution of the gelatin and passed through a 1.5 mm-mesh screen. The granulate thus obtained was dried at 45°C, again passed through the screen, the dry granulate was admixed with the talcum and the magnesium stearate, and the resulting composition was compressed into 300 mgm-pill cores, which were then coated with a thin shell consisting essentially of a mixture of talcum and sugar and finally polished with beeswax. Each coated pill contained 25 mgm of the pentenone compound and was an oral dosage unit composition with effective antiphlogistic action.

EXAMPLE 86

Gelatin capsules

The capsule filler composition is compounded from the following ingredients:

| | | |
|---|---|---|
| 4-(2-Fluoro-4-biphenylyl)-2-butanol | 200.0 | parts |
| Corn starch | 190.0 | " |
| Colloidal silicic acid | 6.0 | " |
| Magnesium stearate | 4.0 | " |
| Total | 400.0 | parts |

Preparation

The ingredients are intimately admixed with each other, and the composition is filled into gelatin capsules of suitable size. Each capsule contains 200 mgm of the butanol compound and is an oral dosage unit composition with effective antiphlogistic action.

EXAMPLE 87

Suppositories

The suppository composition is compounded from the following ingredients:

| | | |
|---|---|---|
| (E)-4-(3-Chloro-4-cyclohexyl-phenyl)-3-pentene-2-ol | 50.0 | parts |
| Suppository base (e.g. cocoa butter) | 1600.0 | " |
| Total | 1650.0 | parts |

Preparation

The pulverized pentenol compound was stirred, by means of an immersion homogenizer, into the molten suppository molds at 38°C and allowed to harden therein. Each suppository contained 50 mgm of the pentanol compound and was a rectal dosage unit composition with effective antiphlogistic action.

EXAMPLE 88

Suspension

The suspension is compounded from the following ingredients:

| | | |
|---|---|---|
| 4-(2-Fluoro-4-biphenylyl)-2-butanol | 4.0 | parts |
| Dioctyl sodium sulfosuccinate (DONSS) | 0.02 | " |
| Benzoic acid | 0.1 | " |
| Sodium cyclamate | 0.2 | " |
| Colloidal silicic acid | 1.0 | " |
| Polyvinylpyrrolidone | 0.1 | " |
| Glycerin | 25.0 | " |
| Grapefruit flavoring | 0.1 | " |
| Distilled water q.s.ad | 100.0 | " |
| | | by vol. |

Preparation

The DONSS, the benzoic acid, the sodium cyclamate and the polyvinylpyrrolidone were dissolved in the distilled water heated to 70°C. The glycerin and silicic acid were then added. The resulting solution was cooled to room temperature, and the pulverized butanol compound was suspended therein by means of an immersion homogenizer. Subsequently, the flavoring was added, and the mixture was diluted with water to the indicated volume. 5 Ml of the suspension contained 200 mgm of the butanol compound and were an oral dosage unit composition with effective antiphlogistic action.

Analogous results are obtained when any one of the other compounds embraced by formula I is substituted for the particular active ingredient in Examples 84 through 88. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

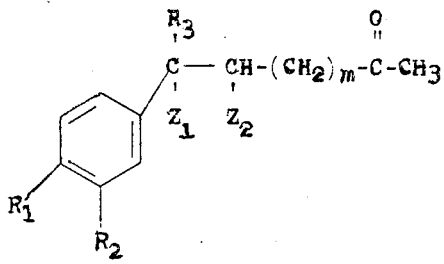

wherein
$R_1$ is phenyl, o-fluoro-phenyl or o-chloro-phenyl,
$R_2$ is hydrogen, fluorine, chlorine or bromine,
$R_3$ is hydrogen, methyl, or ethyl,
$Z_1$ and $Z_2$ are each hydrogen or together form an additional carbon-to-carbon bond, and
$m$ is 2,4,6,8 or, when $R_1$ is halo-phenyl and/or $R_2$ is halogen and/or $R_3$ is methyl or ethyl, also 0.

2. The compound of claim 1 which is 6-(2-fluoro-4-biphenylyl)-2-hexanone.

3. The compound of claim 1 which is 4-(4-biphenylyl)-2-pentanone.

4. The compound of claim 1 which is 8-(2'-fluoro-4-biphenylyl)-2-octanone.

5. The compound of claim 1 which is (E)-4-(4-biphenylyl)-3-pentene-2-one.

6. The compound of claim 1 which is (E)-4-(2'-fluoro-4-biphenylyl)-2-pentene-2-one.

7. The compound of claim 1 which is (E) -4-(2'-fluoro-4-biphenylyl)-3-pentene-2-one.

* * * * *

UNITED STATES PATENT OFFICE
CERTIFICATE OF CORRECTION

Patent No. 3,950,427         Dated April 13, 1976

Inventor(s) WOLFHARD ENGEL, JOSEF NICKL, HELMUT TEUFEL and GUNTHER ENGELHARDT

It is certified that error appears in the above-identified patent and that said Letters Patent are hereby corrected as shown below:

| | |
|---|---|
| Col. 7, line 4 | "ir" should read -- or -- |
| Col. 7, line 7 | "temprature" should read -- temperature -- |
| Col. 13, line 1 | "by" should read -- be -- |
| Col. 15, line 62 | " -alkanophenole" should read -- alkanophenone -- |
| Col. 25, line 41 | " -4-diphenylyl)" should read -- 4-biphenylyl) -- |
| Col. 29, line 14 | "acetophenone 1st ethyl 3rd" should read -- acetophenone and ethyl -- |
| Col. 29, line 15 | "the yield of example, % of theory" should read -- a yield of 19% of theory -- |
| Col. 29, line 18 and 19 | Cancel "toluene, continuously the alcoholate isopropylate" |
| Col. 35, line 45 | "Winder" should read -- Winter -- |

Signed and Sealed this

Sixth Day of July 1976

[SEAL]

Attest:

RUTH C. MASON
Attesting Officer

C. MARSHALL DANN
Commissioner of Patents and Trademarks